US010856774B2

(12) United States Patent
Baltay et al.

(10) Patent No.: US 10,856,774 B2
(45) Date of Patent: *Dec. 8, 2020

(54) OCULAR MICRO TREMOR (OMT) SENSOR, SYSTEM AND METHOD

(71) Applicant: BRAINSTEM BIOMETRICS, INC., Lincoln, MA (US)

(72) Inventors: Michael M Baltay, Lincoln, MA (US); Clark B Foster, Mission Viejo, CA (US); Ciaran Bolger, Dublin (IE); Martin Acquadro, Wellesley, MA (US); Bruce A Rasmussen, Acton, MA (US)

( * ) Notice: Subject to any disclaimer, the term of this patent is extended or adjusted under 35 U.S.C. 154(b) by 443 days.

This patent is subject to a terminal disclaimer.

(21) Appl. No.: 15/784,412

(22) Filed: Oct. 16, 2017

(65) Prior Publication Data

US 2018/0116558 A1     May 3, 2018

Related U.S. Application Data

(63) Continuation of application No. 14/963,177, filed on Dec. 8, 2015, now Pat. No. 9,788,760.

(51) Int. Cl.
*A61B 5/00* (2006.01)
*A61B 5/11* (2006.01)
*A61B 3/113* (2006.01)

(52) U.S. Cl.
CPC ............ *A61B 5/1106* (2013.01); *A61B 3/113* (2013.01); *A61B 5/0004* (2013.01);
(Continued)

(58) Field of Classification Search
CPC ... A61B 5/1106; A61B 5/1103; A61B 5/0004; A61B 5/1126; A61B 5/4064;
(Continued)

(56) References Cited

U.S. PATENT DOCUMENTS 3,948,248 A * 4/1976 Zuckerman ............ A61B 3/165
                                                                600/457
4,863,259 A * 9/1989 Schneider .............. A61B 3/113
                                                                351/210
(Continued)

OTHER PUBLICATIONS

Al-Kalbani et al., "An automated ocular microtremor feature extraction using the gabor thresholding technique," 2007 Annual International Conference of the IEEE Engineering in Medicine and Biology Society: [EMBC '07], 2851-2854 (2007).
(Continued)

*Primary Examiner* — Max F Hindenburg
(74) *Attorney, Agent, or Firm* — Foley Hoag LLP; Hathaway P. Russell; Stephen J. Kenny

(57) ABSTRACT

An eye sensor, system and method for measuring fixational eye movements of an individual's eyeball (e.g., ocular microtremors and microsaccades) to provide a variable voltage biosignal for measuring the individual's brain stem activity. The eye sensor comprises a sensor mounted on the individual's closed or opened eyelid so as to be deflected by the fixational eye movements of the eyeball. A shielded flexible ribbon assembly supplies the biosignal generated by the sensor to an amplifier located on the individual's skin where the biosignal is amplified. The amplifier is interconnected with a signal processor and a display by which graphical and numerical representations of the biosignal are made accessible to an anesthesiologist, intensivist or clinician. A method for analyzing the biosignal to determine the brainstem activity of a patient.

31 Claims, 13 Drawing Sheets

(52) U.S. Cl.
CPC .......... *A61B 5/1101* (2013.01); *A61B 5/1103* (2013.01); *A61B 5/1126* (2013.01); *A61B 5/4064* (2013.01); *A61B 5/6821* (2013.01); *A61B 5/68335* (2017.08); *A61B 5/742* (2013.01); *A61B 5/002* (2013.01); *A61B 2562/0261* (2013.01); *A61B 2562/164* (2013.01); *A61B 2562/222* (2013.01); *A61B 2562/227* (2013.01)

(58) Field of Classification Search
CPC ..... A61B 5/6821; A61B 5/6832; A61B 5/742; A61B 3/113; A61B 5/1101; A61B 5/68335
See application file for complete search history.

(56) References Cited

U.S. PATENT DOCUMENTS

| | | | | |
|---|---|---|---|---|
| 7,011,410 | B2* | 3/2006 | Bolger | A61B 3/113 351/205 |
| 7,959,578 | B2* | 6/2011 | Lonky | A61B 3/113 600/558 |
| 8,025,404 | B2* | 9/2011 | Bolger | A61B 3/113 351/209 |
| 8,944,602 | B2 | 2/2015 | Eberl et al. | |
| 9,788,760 | B2* | 10/2017 | Baltay | A61B 5/68335 |
| 2006/0082727 | A1* | 4/2006 | Bolger | A61B 5/1101 351/209 |
| 2009/0198148 | A1* | 8/2009 | Lonky | A61B 5/163 600/558 |
| 2010/0191156 | A1 | 7/2010 | Sakamoto et al. | |
| 2014/0180161 | A1 | 6/2014 | Bolger et al. | |
| 2018/0116558 | A1 | 5/2018 | Baltay et al. | |

OTHER PUBLICATIONS

Extended European Search Report for EP Application No. 16873870.6 dated Jul. 16, 2019.
International Search Report and Written Opinion for International Application No. PCT/US2016/065679 dated Feb. 17, 2017.
Sheahan et al., "Ocular microtremor measurement system: Design and performance," Medical and Biological Engineering and Computing, 31(3):205-212 (1993).

\* cited by examiner

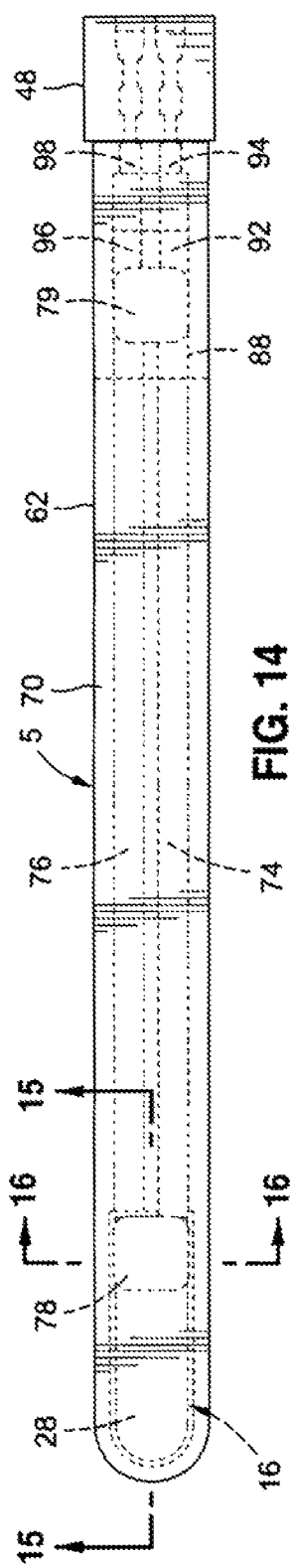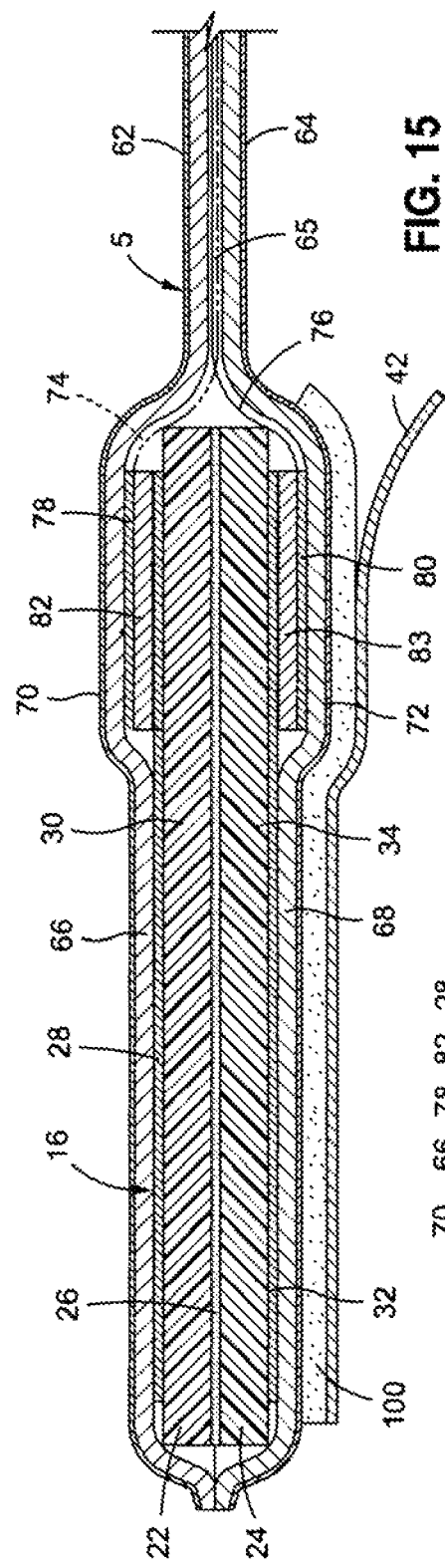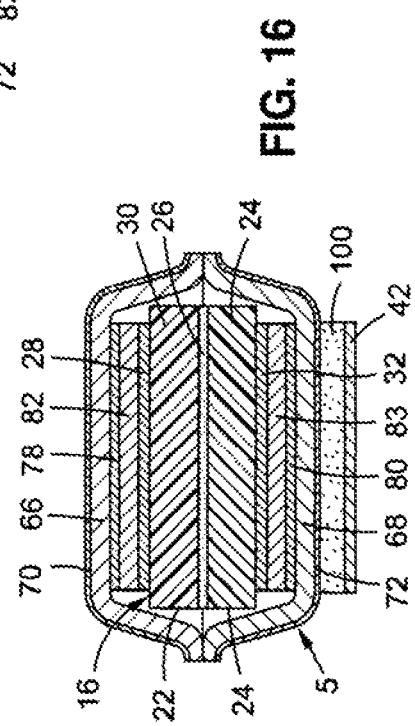

OCULAR MICRO TREMOR (OMT) SENSOR, SYSTEM AND METHOD

BACKGROUND OF THE INVENTION

1. Field of the Invention

This invention relates to an ocular micro tremor (OMT) sensor, system and method which displays graphical and numerical representations of the micromovements of a patient's eyeball (i.e., the cornea/sclera) to provide a healthcare worker (e.g., an anesthesiologist, intensivist or clinician) with an indication of the patient's brain stem activity or altered brain stem state including his level of sedation, consciousness and responsiveness prior to, during and after a medical or clinical procedure, such as, for example, when the patient is anesthetized during an operation. The OMT sensor is thin and compliant and capable of conforming to the shape of the patient's closed eyelid or being located in the tissue folds of the patient's open eyelid at which to be responsive to the micromovements of the patient's eyeball.

2. Background Art

During the performance and treatment of many medical procedures and conditions, an anesthesia is administered so that a patient is sedated and rendered unconscious. In some cases, the patient may be over-sedated throughout an operation which could permanently impact his neural ability and possibly cause brain stem death. In other cases, the patient may be under sedated and immobilized without having the ability to alert medical personnel to a level of consciousness which subjects the patient to pain. In still other cases, over-sedation of a patient may prolong the duration of mechanical ventilation, and under-sedation can result in the patient being subjected to unintended extubation.

For a long time, a primary source of information available to a clinician concerning the depth of anesthesia or sedation was limited to the patient's somatic and autonomic response to physical and/or verbal stimuli. These responses are known to be susceptible to being altered and influenced by neuromuscular blocking drugs, drugs affecting the autonomic nervous system, and the inconsistency of the stimuli. Thus, the presence or absence of these responses does not always accurately correlate with conscious awareness and, therefore, can be inadequate indicators of the depth of the patient's unconscious state.

Sensors are known which are responsive to the micro eye movements of an individual undergoing testing to provide a better indication of the individual's level of sedation and brain stem activity. Sensors are also known which are adhesively bonded over the patient's closed eyelid to sense large (i.e., gross) motions of the patient's eyeball. However, the known sensors are relatively large, such that they are limited to being used during surgery when the eyes of the individual being tested are fully closed and taped shut. Because small micro eye movements have an amplitude of about 500 nanometers, these motions are susceptible to being masked or altered by external electrical and electromagnetic interference as well as physical forces and biological artifacts. Therefore, what is needed now is an improved sensor and a sensor system that are capable of generating a clean biosignal that accurately reflects the ocular micromovements of the patient's eye ball (e.g., having an amplitude of 40 micro meters or less) by reducing unwanted artifacts, both seismic and electrical, and by amplifying the information content of the biosignal without also amplifying the undesirable background noise. Moreover, to maximize its application, the improved sensor should be of low cost, able to avoid contamination and compact so as to be capable of being attached directly to the individual's closed eyelid or in the tissue folds thereof at which to be responsive to the micromovements while the patient is fully or partially asleep or awake and while his eyelid is fully closed, fully open or blinks between being opened and closed. In this same regard, the sensor must be sufficiently compliant so as to avoid applying uncomfortable focused pressure forces to the patient's eye and be easily attached in a convenient manner so as to be worn comfortably with the patient being substantially unaware of its presence.

SUMMARY OF THE INVENTION

In general terms, an ocular micro tremor (OMT) sensor, system and method are disclosed having an application for providing an anesthesiologist, intensivist, clinician, or the like, with a reliable indication of a patient's level of brain stem activity or altered brain stem state including his level of sedation, responsiveness and consciousness prior to, during and following a medical procedure or evaluation such as in the case of an anesthesia administered to the patient during an operation. The OMT sensor includes an electrically active sensing element such as, for example, a flexible piezo-active sensing element that can be attached directly over the patient's closed eyelid or in the tissue folds of his opened eyelid so as to be responsive to the micromotions of the patient's eyeball (i.e., the cornea/sclera) having an amplitude of 40 micro meters or less. The OMT sensor also includes a shielded flexible ribbon assembly by which an alternating voltage biosignal generated by the piezo-active sensing element is supplied to a shielded OMT signal amplifier. The amplified output of the OMT signal amplifier of the OMT sensor is supplied first to a signal processor and then to a visual display which provides graphical and numerical representations of the biosignal and the patient's brain stem activity and level of consciousness.

By way of a preferred embodiment, the flexible piezo-active sensing element of the OMT sensor includes upper and lower thin film piezoelectric layers that are joined one above the other by an intermediate bonding agent. The outside of each of the upper and lower piezoelectric layers has an electrically conductive surface. The piezo-active sensing element of the OMT sensor is adapted to generate the alternating voltage biosignal between the outside conductive surfaces as the upper and lower piezoelectric layers thereof are deflected in response to micromovements of the patient's eyeball. To increase its sensitivity and reduce the discomfort of the wearer, the flexible piezo-active sensing element is attached to the patient's eyelid so as to conform to the shape thereof.

The flexible ribbon assembly of the OMT sensor which extends between the piezo-active sensing element and the OMT signal amplifier includes upper and lower non-conductive strips that are attached one above the other by an intermediate adhesive bonding layer. The flexible ribbon assembly is shielded from external electrical and electromagnetic interference by electrically conductive coatings that lie on the outside of the upper and lower non-conductive strips. An electrically conductive trace runs longitudinally along the inside of each of the upper and lower non-conductive strips such that the traces lie in spaced parallel alignment and in electrical isolation from one another and the electrically conductive shielding coatings. The piezo-active sensing element is sandwiched between the opposing upper and lower non-conductive strips at the proximal end of the flexible ribbon assembly so that the electrically conductive outside surfaces of the sensing element lie in electrical contact with electrical terminals formed at first ends of the conductive traces that run along the upper and lower strips. A flexible circuit board is sandwiched between the opposing upper and lower non-conductive strips at the distal end of the flexible ribbon assembly so as to lie in electrical contact with electrical terminals formed at the opposite ends of the conductive traces. The flexible circuit board at the distal end of the flexible ribbon assembly is coupled to an electrical connector block that is located at the interior of the OMT signal amplifier. Accordingly, the alternating voltage biosignal generated by the piezo-active sensing element of the OMT sensor is supplied to the OMT signal amplifier by way of the electrically conductive traces that run along the upper and lower non-conductive strips of the flexible ribbon assembly.

The OMT signal amplifier of the OMT sensor to which the alternating voltage biosignal is supplied from the flexible piezo-active sensing element and the shielded flexible ribbon assembly includes an electrically conductive housing that shields the biosignal from external electrical and electromagnetic interference. The amplifier housing is attached by an electrically conductive adhesive patch to the patient skin. A printed circuit board which lies at the bottom of and within the amplifier housing is coupled to a grounding electrode that extends through the housing to be held against the patient's skin. The electrically conductive traces which run along the flexible ribbon assembly and carry the OMT biosignal from the sensing element are connected to the printed circuit board for amplification by means of the aforementioned connector block located within the housing of the OMT signal amplifier. First and second electrically conductive mesh pillows lie inside the amplifier housing so as to contact respective ones of the electrically conductive shielding coatings that lie on the outside of the upper and lower non-conductive strips of the ribbon assembly. The mesh pillows lie in circuit paths by which the shielding coatings of the ribbon assembly are connected to each other and to electrical ground at the patient's skin by way of the grounding electrode through the bottom of the amplifier housing. The output of the OMT signal amplifier is supplied from the printed circuit board thereof to the signal processor by way of either a shielded cable from the amplifier housing or a wireless transmitter that is located within the amplifier housing and communicates with a remote transceiver of the signal processor.

BRIEF DESCRIPTION OF THE DRAWINGS

FIG. 14 is a top view of the shielded flexible ribbon assembly of FIG. 13 connected at a proximal end thereof to the multiple layer piezo-active sensing element of FIGS. 8-10 and at a distal end to an electrical connector block of the OMT signal amplifier of FIG. 12;

FIG. 15 is a cross-section of the shielded flexible ribbon assembly taken along lines 15-15 of FIG. 14;

FIG. 16 is a cross-section of the shielded flexible ribbon assembly taken along lines 16-16 of FIG. 14;

DESCRIPTION OF THE PREFERRED EMBODIMENT

Figure 1:
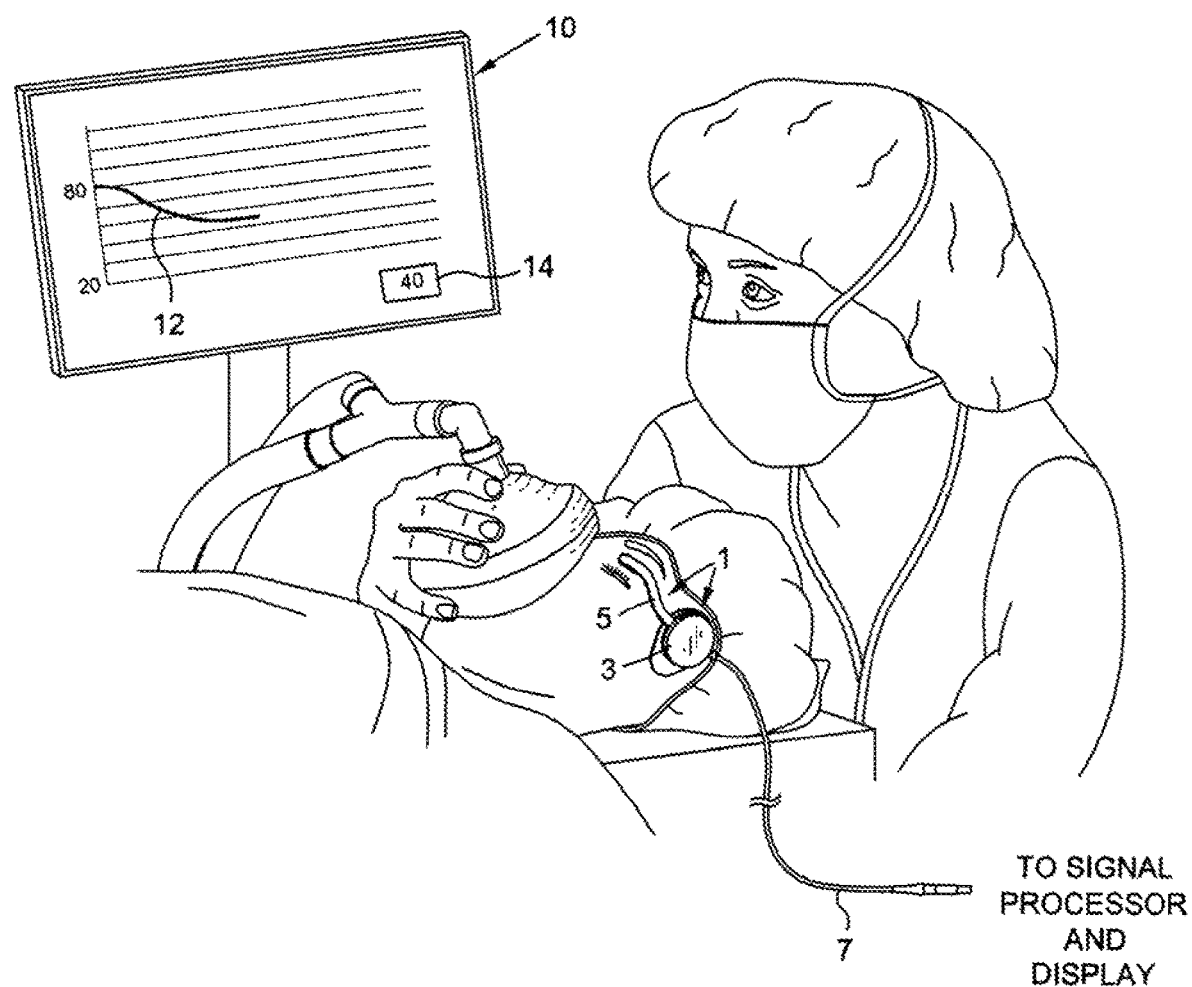
FIG. 1 shows an anesthesiologist watching a display to view graphical and numerical representations of an electrical biosignal which are indicative of the brain stem activity and level of consciousness of a sedated patient who undergoes an operation while wearing the ocular micro tremor (OMT) sensor of the invention.

Referring initially to FIG. 1 of the drawings, there is shown a healthcare practitioner, such as an anesthesiologist, intensivist, clinician, or the like, monitoring a patient who is unconscious and sedated. The (e.g., anesthesiologist) is able to monitor the brain stem activity and altered brain stem state of the patient to measure his level of sedation, consciousness and responsiveness by virtue of a compact, low cost and highly compliant ocular micro tremor (hereinafter "OMT") sensor. The OMT sensor 1 is shown in FIG. 1 positioned at the eyelid of the patient so as to be advantageously able to reliably sense the micro tremors of the patient's eyeball (i.e., micromovements of the cornea/sclera which have an amplitude of 40 micrometers or less) in order to provide the anesthesiologist with an indication of the patient's awareness during a medical procedure (e.g., in an operating room or intensive care facility).

However, it is to be understood that the OMT sensor 1 herein disclosed can also be used to monitor and provide an indication of the alertness, awareness, arousal, diagnosis of injury and behavior modification of an individual in both medical and industrial environments. The OMT sensor 1 is also capable of monitoring any condition or circumstance in which it is desirable to obtain a measurement of brain stem activity of an individual to be compared against a known reference. To this end, the OMT sensor 1 of this invention is advantageously capable of being attached directly over the patient's closed eyelid or in the tissue folds adjacent the patient's eyelid. While the OMT sensor 1 will sometimes be referred to herein as having particular application for use by a patient in the care of an anesthesiologist or similar healthcare practitioner, it is to be once again understood that the sensor can also be used in an industrial or other non-medical environments to test the alertness of one wishing to drive, operate machinery, perform complex tasks, etc.

The OMT sensor 1 of FIG. 1 includes an electrically active sensing element which, according to a preferred embodiment of this invention, is a multi-layer piezo-active sensing element (designated 16 in FIGS. 8-10) that is coupled to an OMT signal amplifier 3 by way of a shielded flexible ribbon assembly 5. The output of the OMT signal amplifier 3 of the OMT sensor 1 is supplied to a signal processor (designated 9 and best shown in FIG. 17) by means of a shielded cable 7. The signal processor, in turn, is electrically connected to a visual display 10. The details of the multiple layer piezo-active sensing element 16, the flexible ribbon assembly 5, as well as the OMT signal amplifier 3 to which the sensing element 16 is coupled to form the OMT sensor 1 will be described in greater detail hereinafter.

FIG. 1 shows the visual display 10 which communicates with the signal processor 9 (of FIG. 17) to display for the anesthesiologist information generated by the OMT sensor 1 when the patient is unconscious and sedated. However, the display 10 can also provide information during a preliminary baseline test when the patient is semi-conscious or fully conscious, alert and not sedated. By way of example only, the display 10 shows an OMT biosignal 12 that is generated by the OMT sensor 1 in response to micromovements of the patient's eyeball. The shape and amplitude of the OMT biosignal 12 provide a graphical representation of the patient's brain stem activity and his level of consciousness over a particular sampling time. The OMT biosignal 12 is generally an alternating voltage waveform that is reflective of the micromovements of the patient's eyeball to which the OMT sensor 1 is responsive by way of the patient's eyelid. In addition, the display 10 also shows a discrete reference number 14 to be computed by the signal processor for easy visual reference by the anesthesiologist. By way of example, the reference number 14 being displayed is dependent upon the micromovements of the eyeball and the corresponding frequency of the waveform of the OMT biosignal 12 in order to provide another indication of the patient's brain stem activity and his level of consciousness, sedation and responsiveness.

Figure 2:
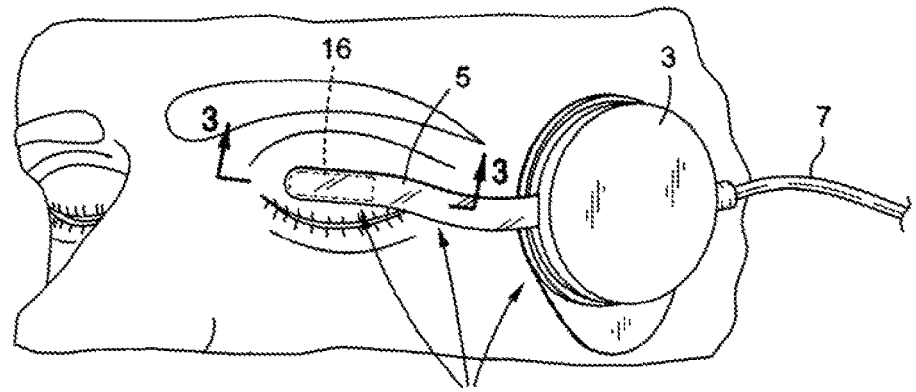
FIG. 2 shows a multiple layer piezo-active sensing element of the OMT sensor of FIG. 1 attached to a closed eyelid of the patient at which to be responsive to micromovements of the patient's eyeball so that the biosignal is generated by the sensing element and supplied to an OMT signal amplifier mounted at the eye.
Figure 3:
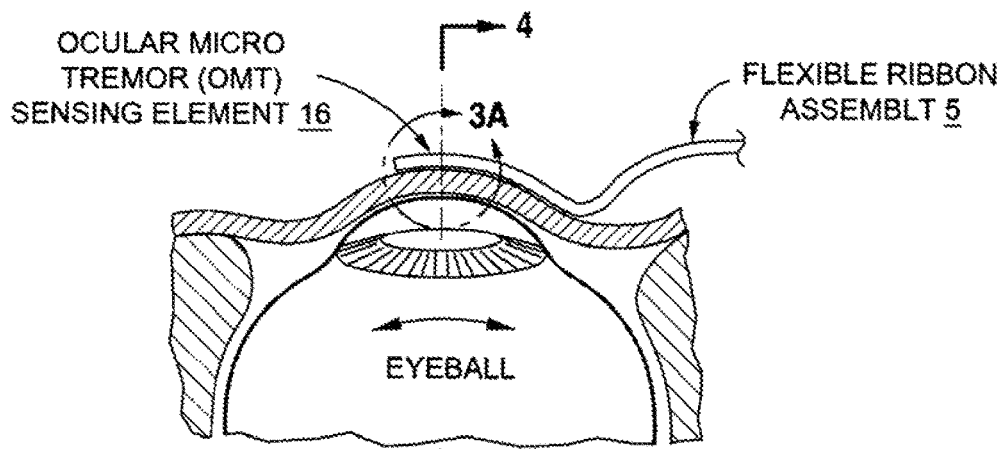
FIG. 3 is a cross-section of the OMT sensor taken along lines 3-3 of FIG. 2.
Figure 4:
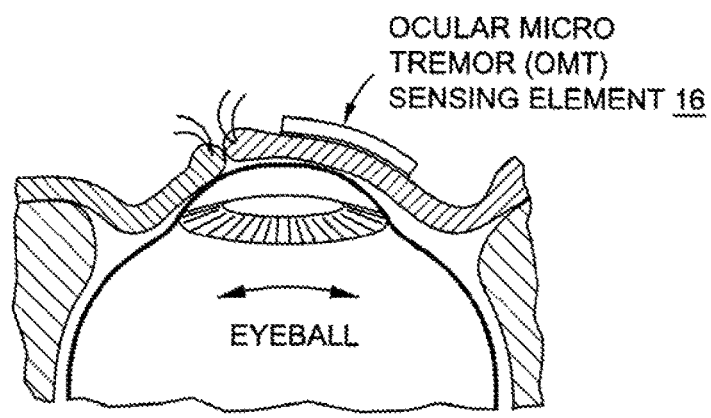
FIG. 4 is a cross-section of the OMT sensor taken along lines 4-4 of FIG. 3.

Turning now to FIGS. 2-4 of the drawings, the multiple layer piezo-active sensing element 16 (of FIGS. 8-10) of the OMT sensor 1 is shown attached to a closed eyelid of an individual, such as a patient who is heavily sedated while undergoing an operation in an operating room. However, and as indicated previously, the OMT sensor 1 can also be attached to the eyelid of an individual undergoing evaluation in an industrial or other non-medical environment. In this case, the patient's eyelid is held closed prior to the attachment of the sensing element 16. A double-sided pressure sensitive adhesive patch (designated 100 in FIGS. 3A and 13) is used to hold the sensing element 16 of the OMT sensor 1 against the patient's closed eyelid above the patient's eyeball at which to be responsive to the micromovements of the eyeball and thereby provide the OMT biosignal 12 (of FIG. 1) by way of the flexible ribbon assembly 5 to the OMT signal amplifier 3. The OMT signal amplifier 3 provides an amplified analog OMT biosignal 12 to the signal processor so that both graphical and numerical representations of the patient's brain stem activity including his level of consciousness, sedation and responsiveness are visually available to the anesthesiologist at the display 10.

However, there are instances when it would be desirable to be able to use the OMT sensor 1 of this invention to measure and indicate the patient's brain stem activity and his level of consciousness when his eyelid is fully or partially open. In this case, and referring to FIGS. 5 and 6 of the drawings, the OMT sensor 1 is shown attached to the patient's rolled up eyelid. For example, it is preferable to use the OMT sensor 1 in the manner shown in FIGS. 5 and 6 at those times when the patient is lightly or moderately sedated, when the patient's eyelid is alternately being opened and closed, or when the patient's eyelid is fully open, such as while a preliminary baseline test is being conducted.

Figure 5:
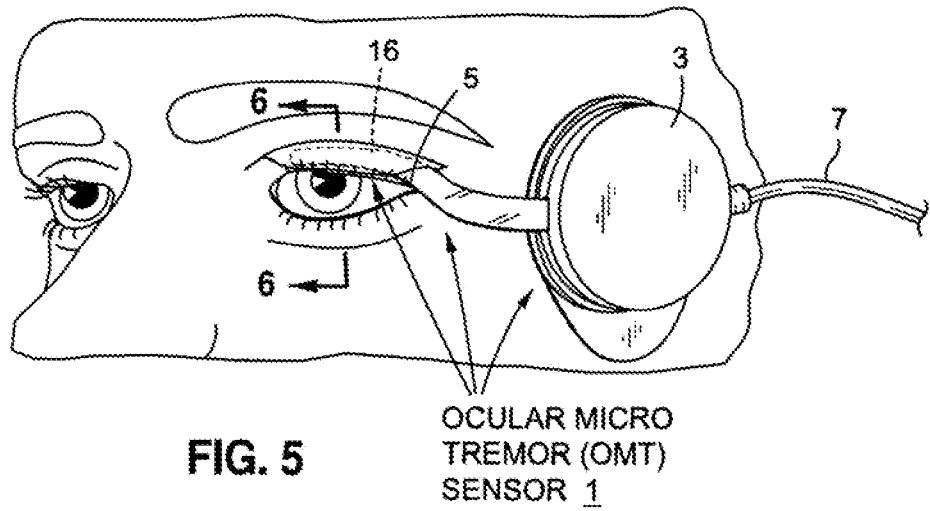
FIG. 5 shows the piezo-active sensing element of the OMT sensor of FIG. 1 located within the tissue folds of the patient's open eyelid at which to be responsive to the micromovements of the patient's eyeball so that the OMT biosignal is generated by the sensing element and supplied to the OMT signal amplifier.
Figure 6:
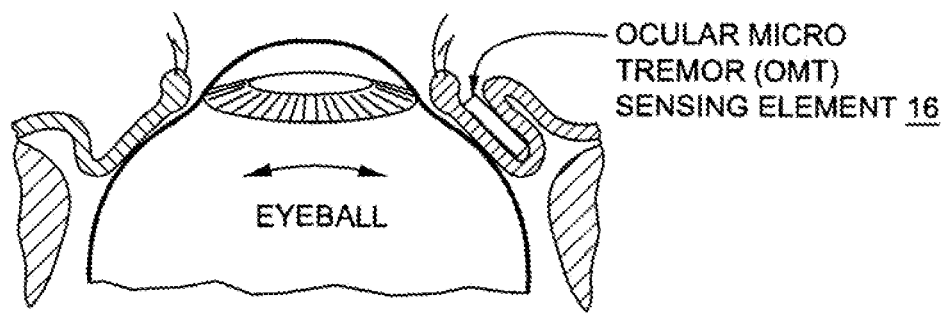
FIG. 6 is a cross-section of the OMT sensor taken along lines 6-6 of FIG. 5.

By virtue of the foregoing, the patient's brain stem activity and level of consciousness can be continuously monitored to enable intervention by the anesthesiologist or other healthcare practitioner when necessary prior to, during and following a medical procedure (e.g., an operation) when the patient will be sedated for some portion of the procedure. Because the OMT sensor 1 including the multiple layer piezo-active sensing element 16 (of FIGS. 8-10) and the flexible ribbon assembly 5 is thin and compliant, the sensor 1 may be advantageously attached, as shown in FIGS. 5 and 6, between the tissue folds of the patient's opened eyelid at which the piezo-active sensing element 16 of sensor 1 is responsive to the micromovements of the patient's eyeball.

Figure 7:
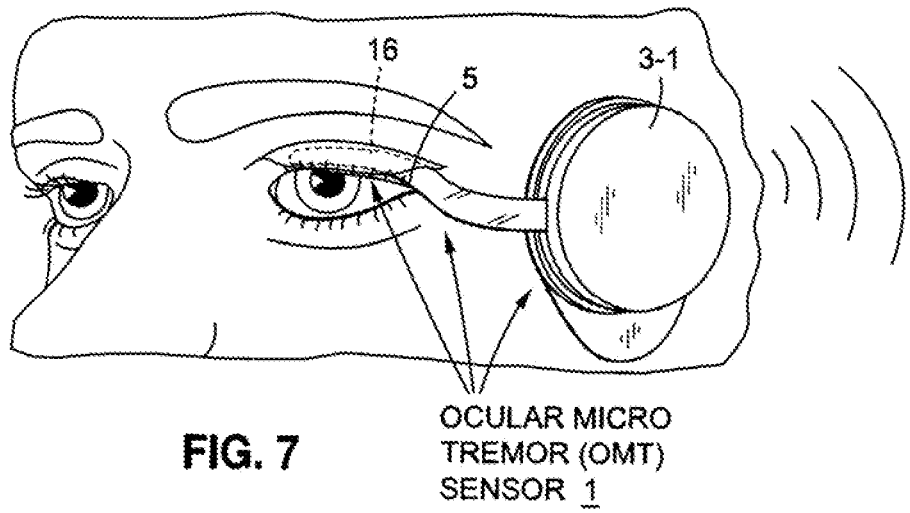
FIG. 7 shows the OMT sensor of FIG. 5 including a wireless OMT signal amplifier.

In FIGS. 1-6, the OMT signal amplifier 3 of the OMT sensor 1 has been described as being connected to a signal processor (designated 9 in FIG. 17) by means of a shielded cable 7. However, as shown in FIG. 7 of the drawings, it is within the scope of this invention for the amplifier 3 to be replaced by a wireless OMT signal amplifier 3-1. In this case, the shielded cable (designated 7 in FIG. 5) will now be eliminated. Moreover, the wireless OMT signal amplifier 3-1 is provided with an analog-to-digital converter (designated 110 in FIG. 18) and a conventional wireless transmitter (designated 116 in FIG. 18), and the signal processor (designated 9-1 in FIG. 18) is provided with a complementary transceiver 118. In this manner, the amplified OMT biosignal can be transmitted from the OMT signal amplifier 3-1 to the signal processor 9-1 at a remote location and over a wireless communication path.

Figure 8:
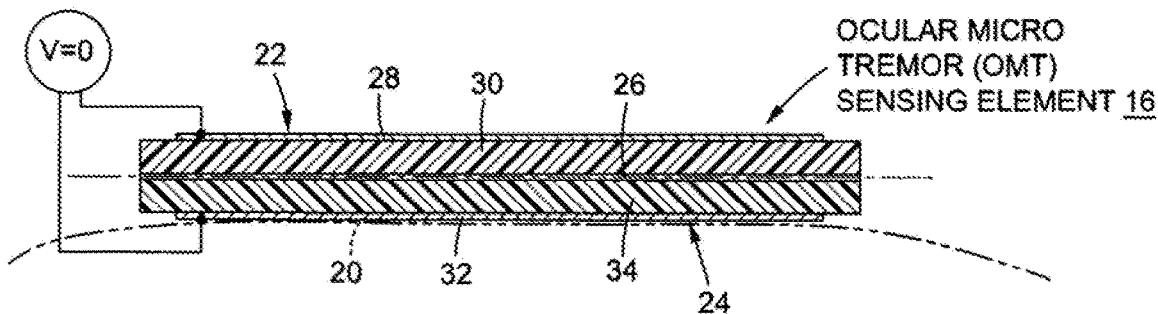
FIG. 8 shows a preferred embodiment for the multiple layer piezo-active sensing element of the OMT sensor of FIG. 1 which is deflected in response to the micromovements of the patient's eyeball to which the sensing element is responsive in order to generate the OMT biosignal.
Figure 9:
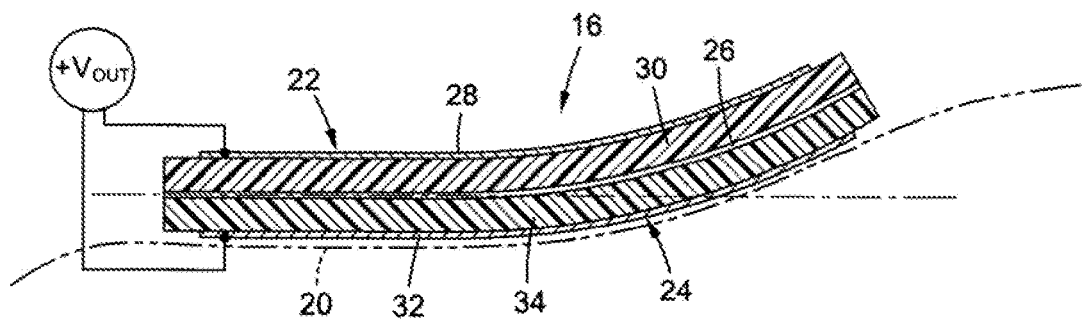
FIGS. 9 and 10 show the multiple layer piezo-active sensing element of FIG. 8 being deflected in different directions to generate the OMT biosignal depending upon the direction of the micromovements of the patient's eyeball.
Figure 10:
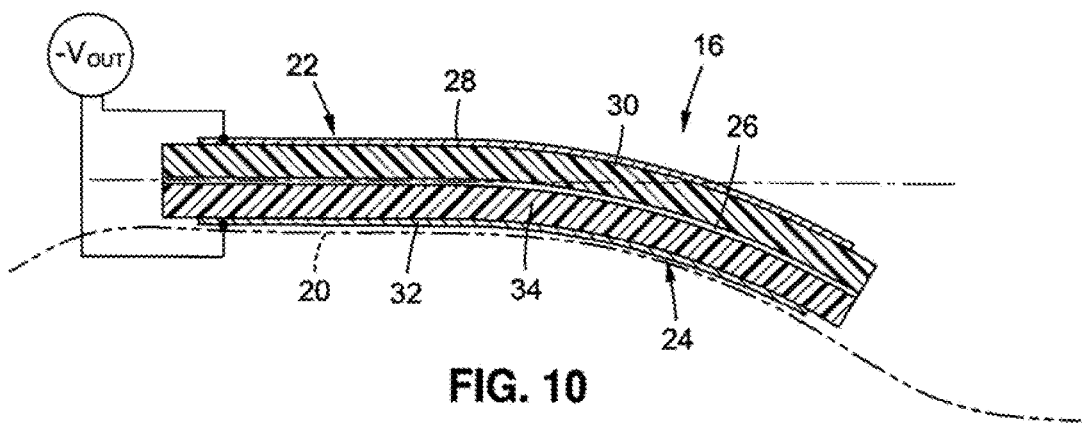

Details of the multiple layer piezo-active sensing element 16 of the ocular micro tremor (OMT) sensor 1 shown in FIGS. 1-6 are now disclosed while referring to FIGS. 8-10 of the drawings. As was previously explained, the sensing element 16 of the OMT sensor 1 is adhesively held against the moving surface of the patient's opened or closed eyelid (represented generally by reference numeral 20 in FIGS. 8-10) so as to be responsive to the micromovements of the patient's eyeball which have an amplitude of 40 micro meters or less and thereby provide a corresponding alternating voltage OMT biosignal to the soon-to-be-described OMT signal amplifier (designated 3 in FIG. 1).

According to the preferred embodiment, the multiple layer piezo-active sensing element 16 of the OMT sensor 1 has a thin planar top layer 22, a thin planar bottom layer 24 and an intermediate bonding agent 26 (e.g., epoxy) located therebetween to hold the top and bottom layers 22 and 24 together one above the other. A first electrically conductive (e.g., copper) surface 28 is applied to the outside of a first flexible piezoelectric (e.g., PVDF) film 30 from the planar top layer 22 of the piezo-active sensing element 16 to establish a first output terminal. A second electrically conductive (e.g., copper) surface 32 is applied to the outside of a second flexible piezoelectric film 34 from the planar bottom layer 24 of sensing element 16 to establish a second output terminal. The inside of each of the first and second piezoelectric films 30 and 34 of the top and bottom layers 22 and 24 of sensing element 16 which face one another are held in opposing alignment by the intermediate bonding agent 26.

The length and width of the piezoelectric films 30 and 34 may be larger than the respective length and width of the first and second conductive surfaces 28 and 32 so as to avoid undesired electrical communication between the surfaces 28 and 32. The ideal thickness of the multiple layer piezo-active sensing element 16 shown in FIGS. 8-10 is between 20 to 150 microns.

The first and second flexible piezoelectric films 30 and 34 of the thin planar top and bottom layers 22 and 24 of the piezo-active sensing element 16 of the OMT sensor 1 are conventional and are adapted to generate a voltage as the sensing element is deflected in response to the micromovements of the patient's eyeball which create a corresponding motion through the eyelid 20 above which the sensing element 16 is attached. That is to say, the normally planar first and second piezoelectric films 30 and 34 are deformed and deflected by the movements of the patient's eyelid 20 caused by the micromovements of the eyeball. In the case where the multiple layer piezo-active sensing element 16 is at rest as shown in FIG. 8, no voltage is generated by the piezoelectric films 30 and 34 between the first and second output terminals at the outside conductive surfaces 28 and 32. In the case where the piezo-active sensing element 16 is deflected in a first direction by the movement of the patient's eyelid 20 in the same first direction as shown in FIG. 9, a positive voltage is generated by the piezoelectric films 30 and 34 between the output terminals at the outside conductive surfaces 28 and 32. In the case where the sensing element 16 is deflected in an opposite direction by the movement of the patient's eyelid 20 in the same opposite direction as shown in FIG. 10, a negative voltage is generated by the piezoelectric films 30 and 34 between the output terminals at the outside conductive surfaces 28 and 32.

Because the micromovements of the patient's eyeball typically occur at a high frequency and with a variable intensity, the multiple layer piezo-active sensing element 16 of the OMT sensor is likely to flex back and forth at a correspondingly high frequency. The amplitude, positive or negative direction, and frequency of the micromovements to which the sensing element 16 is responsive are reflected graphically and numerically by the OMT biosignal 12 and the reference number 14 that are visually accessible to the anesthesiologist at the display 10 of FIG. 1.

The preferred electrically active sensing element for the OMT sensor 1 has been described while referring to FIGS. 8-10 as being a flexible multi-layer piezo-active sensing element 16 that is adapted to generate a voltage in response to the sensing element being deflected by the micromovements of the patient's eyeball. However, the sensing element of the OMT sensor 1 may also be other electrically active devices, such as a variable resistance element (e.g., a strain gauge), a variable capacitor, accelerometer or a variable inductor, the outputs of which will be indicative of the micromovements of the eyeball of the individual undergoing testing. What is more, it is to be expressly understood that the pair of flexible piezoelectric films 30 and 34 of the multi-layer piezo-active sensing element 16 can be replaced by a single flexible piezoelectric film that has at the top and bottom thereof electrically conductive surfaces which lie thereon to establish the aforementioned first and second output terminals between which the OMT biosignal is generated. The aforementioned single piezoelectric film may be seated on a supportive non-conductive substrate.

In one case, it has been found that attaching a conventional ocular micro tremor sensor to a patient's eyelid may result in a focused pressure being applied to the eyelid which creates a depression in the patient's eyeball. The sometimes intrusive nature of the conventional sensor applying a focused pressure to the patient's eyeball can, over time, cause patient discomfort. In this and other cases, a conventional sensor may require additional intervention and controls to ensure its proper position placement in order to be capable of responding to the patient's eye motions. What is even more, the patient may resist wearing the conventional sensor to avoid the discomfort caused by the pressure being applied to his eyeball.

Figure 3A:
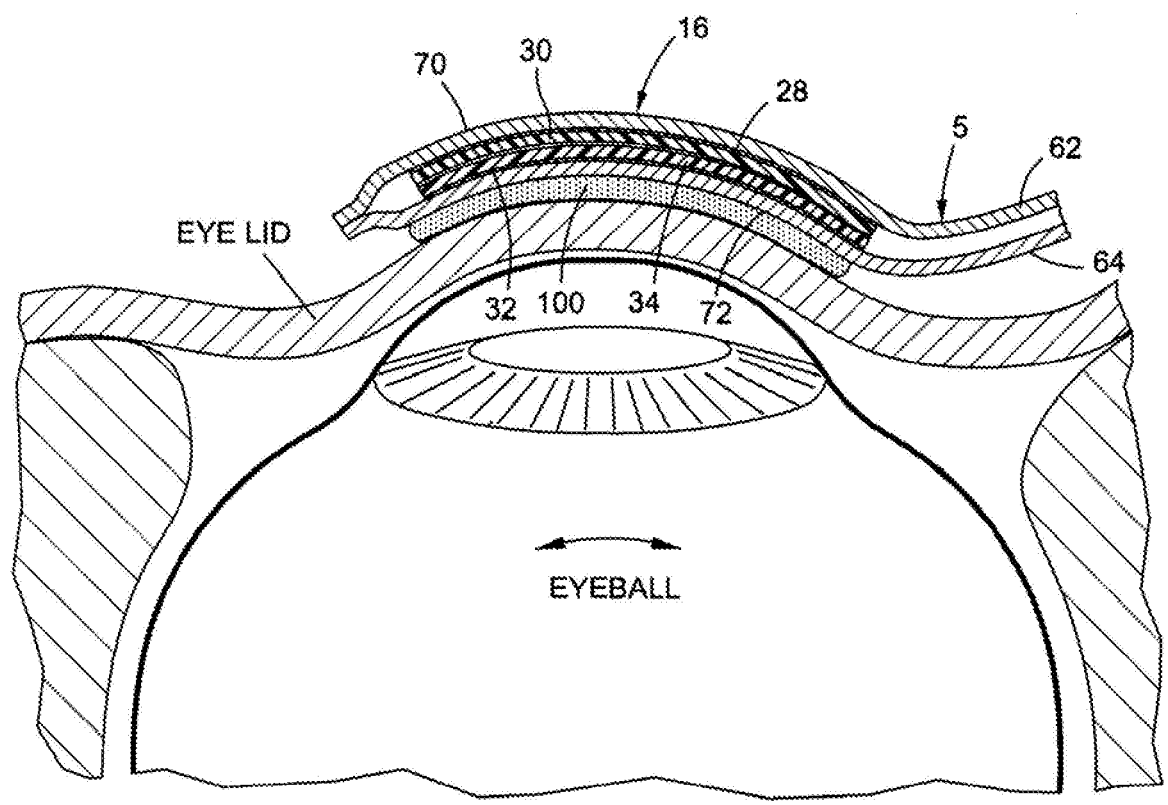
FIG. 3A is an enlarged detail taken from FIG. 3 showing the multiple layer piezo-active sensing element of the OMT sensor lying on the closed eyelid of the patient.

Referring specifically to FIGS. 3 and 3A of the drawings, the ideal position is described at which the flexible multi-layer piezo-active sensing element 16 of the OMT sensor 1 shown in FIGS. 8-10 is held against the patient's fully closed eyelid. As an important feature of the invention, the flexible sensing element 16 is sufficiently thin (as explained when referring to FIGS. 8-10) and compliant to assume a generally arcuate (i.e., curved) configuration in order to conform to the shape of the patient's eyelid when the sensing element is attached thereto by means of the double-sided pressure sensitive adhesive patch 100. That is, the sensing element 16 surrounds at least some of the patient's closed eyelid and is sized so as to be large enough to cover angular excursions of the eyeball yet small enough to be placed within the eye socket.

In this regard, the top and bottom planar layers 22 and 24 of the piezo-active sensing element 16 of the OMT sensor 1 of this invention will cover a relatively large surface area of the eyelid so as to be responsive to a full range of motion of the patient's eyeball transmitted through the eyelid. Moreover, the pressure applied to the eyelid by the sensing element 16 is more uniformly distributed around the eyelid than conventional focused pressure sensing elements. Accordingly, the flexible piezo-active sensing element 16 will be more comfortable to wear for longer periods, is less costly and easier to accurately position at the eyelid to achieve a reliable response than conventional focused pressure sensing elements. Therefore, the OMT sensor 1 can be comfortably fitted to the patient such that the sensing element 16 thereof is unlikely to be noticed or objected to.

The flexible multiple layer piezoelectric sensing element 16 is shown in FIG. 3A conforming to the shape of the patient's eyelid and being coupled to the flexible ribbon assembly 5 of the OMT sensor 1. As will be described in greater detail when referring to FIGS. 16-18, the sensing element 16 is surrounded by upper and lower strips 62 and 64 of the ribbon assembly 5. Electrically conductive coatings 70 and 72 lay over the outside surfaces of respective ones of the upper and lower strips 62 and 64 to provide the ribbon assembly 5 with shielding in order to avoid subjecting the biosignal generated by the sensing element 16 and transmitted via the flexible ribbon assembly 5 to electrical and electromagnetic noise and other interference.

Figure 11:
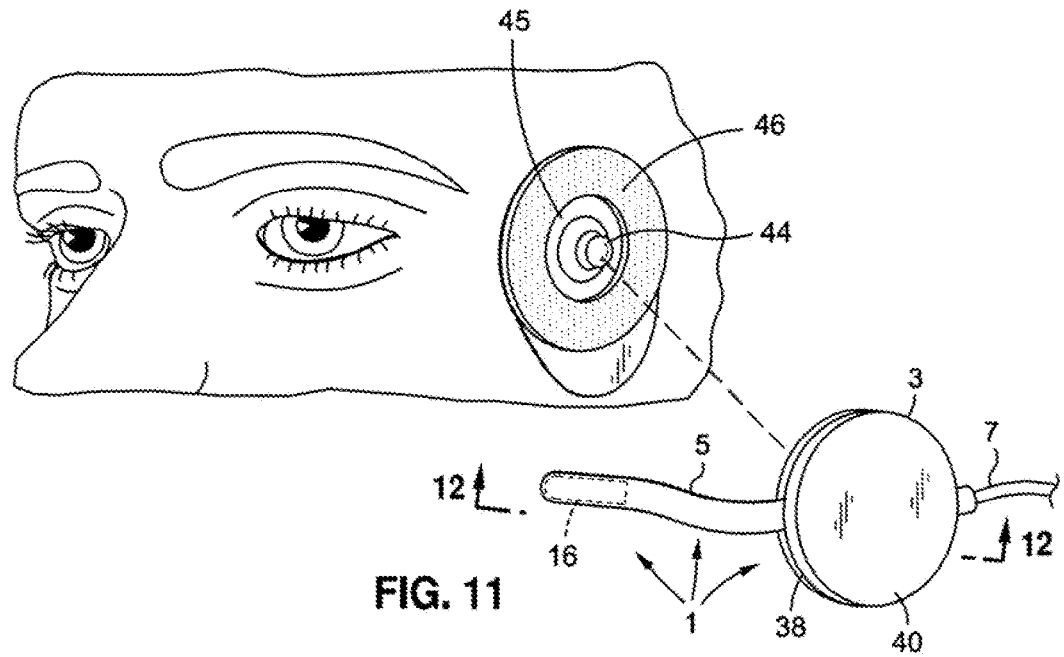
FIG. 11 shows the OMT signal amplifier of the OMT sensor of FIG. 2 being detachably connected to a grounding electrode that is attached by an electrically conductive adhesive patch to the patient's skin.
Figure 12:
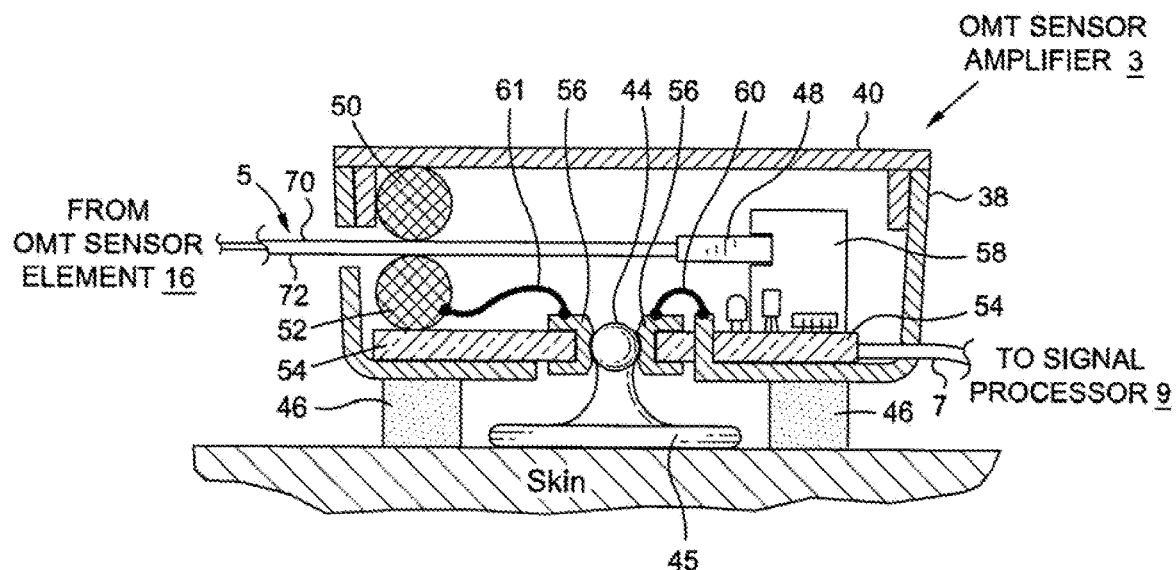
FIG. 12 is a cross-section of the OMT signal amplifier taken along lines 12-12 of FIG. 11.

The details of the OMT signal amplifier 3 of the OMT sensor 1 to which the OMT biosignal that is generated by the multiple layer piezo-active sensing element 16 is supplied are described while referring to FIGS. 11 and 12 of the drawings. To isolate the electrical components of the amplifier 3 and thereby prevent environmental electrical and electromagnetic interference from altering the information contained by the OMT biosignal, the OMT signal amplifier 3 is provided with a conductive shielded housing 38 having a removable lid 40. The multiple layer piezo-active sensing element 16 of the OMT sensor 1 is electrically connected to the amplifier 3 by way of the shielded flexible ribbon assembly 5 (best shown in FIGS. 13-16). It is preferable that the flexible ribbon assembly 5 be given slack and/or be loosely connected between the piezo-active sensing element 16 and the OMT signal amplifier 3 so as to avoid applying loads or pulling forces to the patient's eyelid and thereby inducing a possible unintended response by the sensing element 16.

An amplifier grounding electrode 44 having a flat conductive base 45 is held against the patient's skin by an electrically conductive adhesive foam patch 46 (e.g., a common EKG electrode patch) that is attached to the bottom of the amplifier housing 38 and covered by a pull-off release film strip (not shown). Once the release strip is removed, the adhesive patch 46 is attached to the patient's skin (e.g., at one side of his forehead) so that the OMT signal amplifier 3 will be located adjacent the piezo-active sensing element 16 and thereby avoid applying a pulling force against the ribbon assembly 5. An electrical receptacle 56 inside the amplifier housing 38 is then snapped into detachable mating engagement with the amplifier electrode 44 so that the base 45 of electrode 44 lies flush against the patient's skin. The adhesive patch 46 anchors the OMT signal amplifier 3 in place against the patient's skin and prevents a displacement thereof relative to the ribbon assembly 5 during the period when the patient's ocular micromovements are being monitored. It should be recognized that other conventional electrical and mechanical amplifier attachment means can be substituted for the electrically conductive adhesive foam patch 46.

To ensure that the amplified alternating voltage signals generated by the OMT signal amplifier 3 are not altered by the environment, it is important that both the electrically conductive housing 38 of the OMT signal amplifier 3 and the electrically conductive shielding coatings 70 and 72 that cover the outside surfaces of the upper and lower strips 62 and 64 of the flexible ribbon assembly 5 are connected to electrical ground. To this end, electrical paths are established to ground from the coatings 70 and 72 of the flexible ribbon assembly 5 and the housing 38 of the amplifier 3 to the patient's skin at the amplifier grounding electrode 44 which is held in place against the skin by the electrically conductive adhesive patch 46. Details of these electrical paths to ground at the patient's skin are described below.

As is best shown in FIG. 12, the shielded flexible ribbon assembly 5 of the OMT sensor 1 is connected at a proximal end thereof to the multiple layer piezo-active sensing element 16 (best shown in FIG. 13) and at the opposite distal end to an electrical connector block 48 that is located at the interior of the amplifier housing 38. A first electrically conductive (e.g., mesh) and resilient pillow 50 is positioned within housing 38 so as to lie between the removable lid 40 thereof and the electrically conductive shielding coating 70 that runs over the top of the ribbon assembly 5. A second electrically conductive and resilient pillow 52 is positioned within housing 38 so as to lie between the electrically conductive coating shielding 72 that runs over the bottom of the ribbon assembly 5 and a printed circuit board 54 that is positioned at the bottom of the housing 38 of the OMT signal amplifier 3. The aforementioned amplifier grounding electrode 44 is detachably connected to the signal amplifier 3 through the bottom of housing 38 and to the printed circuit board 54 at the electrical receptacle 56, such that the flat conductive base 45 of electrode 44 is connected to ground against the patient's skin.

The first and second electrically conductive pillows 50 and 52 lie in electrical contact with respective ones of the aforementioned electrically conductive shielding coatings 70 and 72 at the top and bottom of the flexible shielded ribbon assembly 5. Thus, the electrically conductive shielding coating 70 at the top of the flexible ribbon assembly 5 is connected to ground at the patient's skin by way of a first electrical path to ground that includes the first conductive pillow 50, the electrically conductive shielded amplifier housing 38, a first jumper wire 60 that connects housing 38 to the electrical receptacle 56, and finally the amplifier grounding electrode 44 and the electrode base 45 lying against the patient's skin. The electrically conductive shielding coating 72 at the bottom of the flexible ribbon assembly 5 is also connected to ground by way of a second electrical path to ground that includes the second conductive pillow 52 and a second jumper wire 61 that connects pillow 52 to the electrical receptacle 56, and finally the amplifier grounding electrode 44 and the base 45 thereof against the user's skin. In this same regard, it may be appreciated that the conductive shielding coatings 70 and 72 at the top and bottom of the flexible ribbon assembly 5 are electrically connected to one another by way of the electrically conductive mesh pillows 50 and 52 and the electrically conductive shielded amplifier housing 38.

The resilient characteristic of the electrically conductive (e.g., mesh) pillows 50 and 52 which overlay the electrically conductive shielding coatings 70 and 72 of the flexible ribbon assembly 5 accommodate and absorb bending forces to which the ribbon assembly is subjected. The pillows 50 and 52 also support the ribbon assembly 5 within the amplifier housing 38 and suspend the ribbon assembly above the printed circuit board 54 so as to lie in axial alignment with the electrical connector block 48. The electrical connector block 48 to which the distal end of the ribbon assembly 5 is connected is, in turn, electrically connected to the printed circuit board 54 by way of an upstanding connector post 58. The printed circuit board 54 contains conventional signal conditioning and amplifier circuitry by which the OMT alternating voltage biosignal carried by the flexible ribbon assembly 5 is amplified (ideally by a factor of at least ten). An amplified analog OMT biosignal is supplied from the OMT signal amplifier 3 shown in FIG. 12 to the signal processor and display of FIG. 17 by means of the shielded output cable 7 that extends from the printed circuit board 54 and outwardly through a side of the amplifier housing 38. However, as earlier explained the OMT biosignal may also be transmitted from the amplifier to the signal processor over a wireless communication path illustrated in FIG. 18.

Referring concurrently to FIGS. 13-16 of the drawings, details are now provided of the shielded flexible ribbon assembly 5 which is electrically connected at the proximal end thereof to the multiple layer piezo-active sensing element 16 (previously described while referring to FIGS. 8-10) and at the opposite distal end to the OMT signal amplifier 3 (as described while referring to FIG. 12). The flexible ribbon assembly 5 is disposed in surrounding engagement with and connected between the first and second (i.e., top and bottom) electrically conductive surfaces 28 and 32 of the piezo-active sensing element 16 and the electrical connector block 48 that is held (by the connector post 58) above the printed circuit board 54 that is positioned inside and at the bottom of the shielded housing 38 of the OMT signal amplifier 3 shown in FIG. 12.

The shielded ribbon assembly 5 of the OMT sensor 1 includes upper and lower elongated and compliant strips 62 and 64 that are attached one above the other. By way of example, the bottom of the upper strip 62 and the top of the lower strip 64 are bonded face-to-face one another by a conventional thin layer of adhesive (designated 65 in FIG. 15). Each of the upper and lower strips 62 and 64 of ribbon assembly 5 includes a layer 66 and 68 that is manufactured from an electrical insulating polyimide or any other suitable non-conductive material. Both the top and the bottom of each of the non-conductive layers 66 and 68 of the upper and lower strips 62 and 64 are initially covered by an electrically conductive (e.g., aluminum or gold) coating.

As is best shown in FIG. 15, the conductive coatings 70 and 72 which cover the outwardly facing top of the non-conductive layer 66 of the upper strip 62 and the outwardly facing bottom of the non-conductive layer 68 of the lower strip 64 of the flexible ribbon assembly 5 are left intact to create shielding surfaces. The shielding coatings 70 and 72 were previously described while referring to FIG. 12 as being connected to each other and to ground at the individual's skin to shield the ribbon assembly 5 against electrical and electromagnetic energy that might interrupt or distort the biosignal generated by the piezo-active sensing element 16 of the OMT sensor 1 and supplied to the OMT amplifier 3 by ribbon assembly 5.

Figure 13:
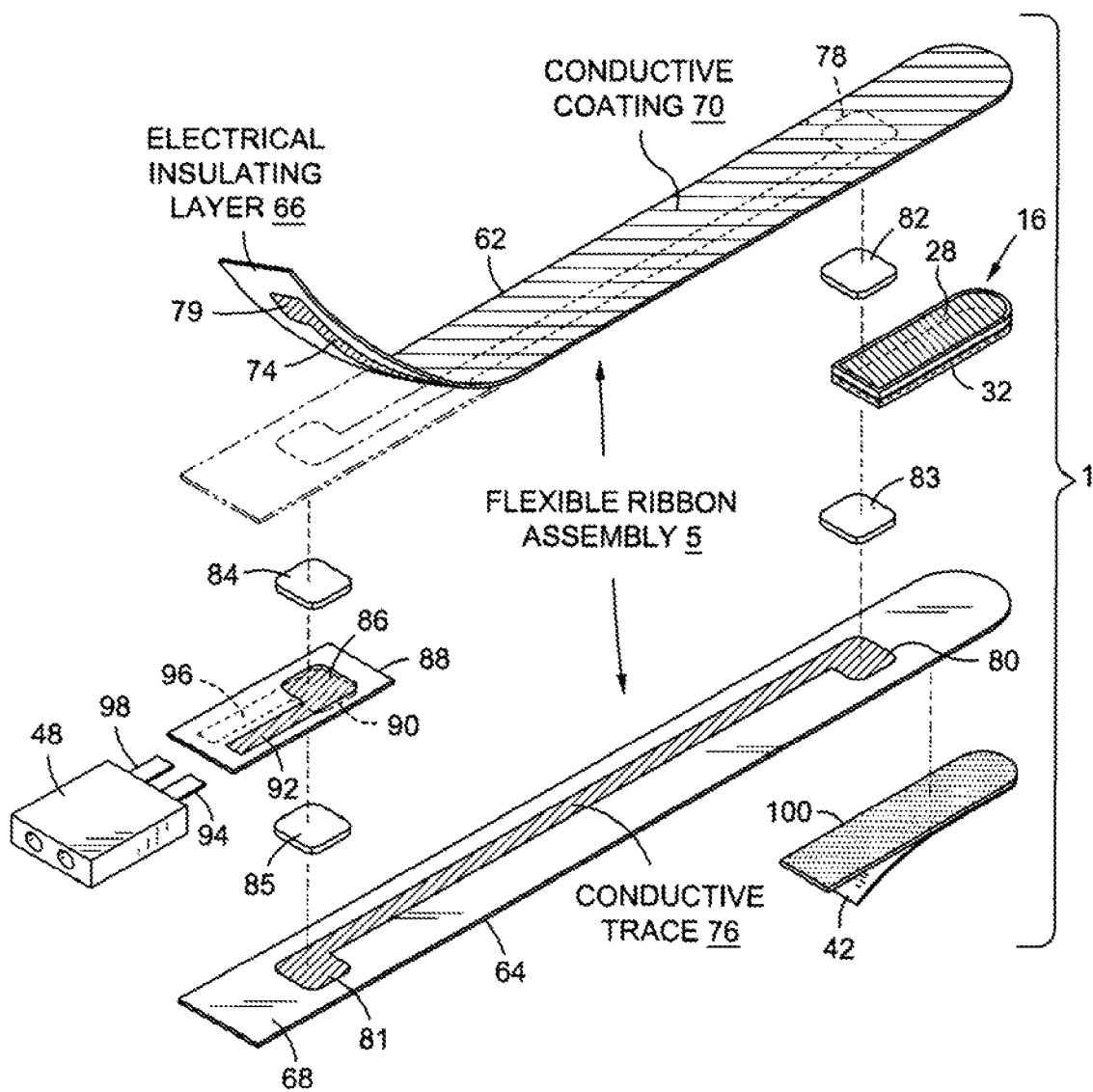
FIG. 13 is an exploded view of a shielded flexible ribbon assembly of the OMT sensor by which the multiple layer piezo-active sensing element of FIGS. 8-10 is electrically connected to the OMT signal amplifier of FIG. 12.

As is best shown in FIG. 13, portions of the conductive coatings which initially cover the inwardly facing bottom of the non-conductive layer 66 of the upper strip 62 and the opposing inwardly facing top of the non-conductive layer 68 of the lower strip 64 are etched away to leave respective longitudinally extending electrically conductive traces 74 and 76 running along the non-conductive layers 66 and 68 of the upper and lower strips 62 and 64. During the aforementioned etching process, pairs of relatively wide electrically conductive terminals 78, 79 and 80, 81 are formed at first and opposite ends of each of the conductive traces 74 and 76. With the upper and lower strips 62 and 64 of the shielded ribbon assembly 5 bonded together by the intermediate adhesive layer 65 (of FIG. 15), the longitudinally extending electrically conductive traces 74 and 76 formed on the bottom and on the top of the opposing insulating layers 66 and 68 of the upper and lower strips 62 and 64 lie in parallel alignment and in electrical isolation from one another. The aforementioned etching process is a preferred technique for forming the electrically conductive traces 74 and 76. However, it should be understood that other conventional techniques can be used to form the traces 74 and 76 on the electrically insulating layers 66 and 68.

As is best shown in FIG. 15, the multi-layer piezo-active sensing element 16 is sandwiched between first ends of the upper and lower strips 62 and 64 at the proximal end of the flexible ribbon assembly 5. More particularly, a first electrically conductive pad 82 is adhesively bonded between the terminal 78 formed at a first end of the trace 74 on the bottom of the upper strip 62 and the first electrically conductive surface 28 at the top of the piezo-active sensing element 16. A second electrically conductive pad 83 is adhesively bonded between the second electrically conductive surface 32 which lies at the bottom of the piezo-active sensing element 16 and the terminal 80 formed at a first end of the trace 76 on the top of the lower strip 64. The terminals 78 and 80 at the first ends of traces 74 and 76 and the first and second conductive pads 82 and 83 on the top and the bottom of the sensing element 16 are all aligned with one another in a stack at the proximal end of the flexible ribbon assembly 5.

A third electrically conductive pad 84 is adhesively bonded between the terminal 79 formed at the opposite end of the trace 74 on the bottom of the upper strip 62 and an opposing upper terminal 86 formed on the top of a flexible transition circuit board 88 (of FIG. 13). The circuit board 88 is sandwiched between opposite ends of the upper and lower strips 62 and 64 at the distal end of the flexible ribbon assembly 5. A fourth electrically conductive pad 85 is adhesively bonded between the terminal 81 formed at the opposite end of the trace 76 on the top of the lower strip 64 and an opposing lower terminal 90 formed on the bottom of the flexible transition circuit board 88. The terminals 79 and 81 at the opposite ends of the traces 74 and 76, the third and fourth conductive pads 84 and 85 above and below the circuit board 88, and the opposing upper and lower terminals 86 and 90 of the circuit board 88 are all aligned with one another in a stack at the distal end of the flexible ribbon assembly 5.

The upper terminal 86 of the transition circuit board 88 (i.e., a first output terminal of the ribbon assembly 5) is electrically connected to the electrical connector block 48 that is surrounded by the electrically conductive shielded housing 38 of the OMT signal amplifier 3 (of FIG. 12) by way of a first conductive trace 92 lying on the top of circuit board 88 and a first electrical contact 94 of connector block 48. The lower terminal 90 of the transition circuit board 88

(i.e., a second output terminal of the ribbon assembly 5) is electrically connected to the connector block 48 by way of a second conductive trace 96 lying on the bottom of circuit board 88 and a second electrical contact 98 of connector block 48. As was previously explained while referring to FIG. 12, the electrical connector block 48 is electrically connected to the printed circuit board 54 that lies at the bottom of the housing 38 of OMT signal amplifier 3. Therefore, it may be appreciated that the alternating voltage biosignal generated by the multiple layer piezo-active sensing element 16 of the OMT sensor 1 is transmitted from the first and second electrically conductive surfaces 28 and 32 at the top and at the bottom of sensing element 16 to the OMT signal amplifier 3 by way of the electrically conductive traces 74 and 76 which run along the upper and lower strips 62 and 64 between the proximal and distal ends of the shielded flexible ribbon assembly 5.

It may be appreciated that the electrically conductive trace 74 which runs along the bottom of the insulating layer 66 of the upper strip 62 of the flexible ribbon assembly 5 is electrically isolated from the shielding coating 70 that covers the top of the insulating layer 66. Likewise, the electrically conductive trace 76 which runs along the top of the insulating layer 68 of the lower strip 64 of the flexible ribbon assembly 5 is electrically isolated from the shielding coating 72 that covers the bottom of the insulating layer 68. Moreover, the shielding coatings 70 and 72 that cover the top of the insulating layer 66 and the bottom of the insulating layer 68 of the upper and lower strips 62 and 64 completely surround the ribbon assembly 5 and enclose the electrically conductive traces 74 and 76 thereof as well as the piezo-active sensing element 16 lying therebetween so as to avoid an alteration of the alternating voltage biosignal as could be caused by external electrical and electromagnetic interference.

The previously mentioned double-sided pressure sensitive adhesive patch 100 is attached at one side thereof to the outwardly facing bottom of the lower strip 64 of the flexible shielded ribbon assembly 5. The opposite side of the adhesive patch 100 is covered by pull off release film strip 42. When the release strip 42 is pulled off and removed from the adhesive patch 100, the OMT sensor 1 including the flexible ribbon assembly 5 and the multi-layer piezo-active sensing element 16 that is sandwiched between the upper and lower strips 62 and 64 at the proximal end of ribbon assembly 5 can be adhesively attached to the patient's eyelid in the manner described above while referring to FIGS. 2-6 to permit the ocular micromotions of the eyeball of the patient to be sensed, amplified, processed and displayed.

By virtue of the shielded flexible ribbon assembly 5 herein disclosed, the multiple layer piezo-active sensing element 16 can be substantially isolated from mechanical forces that might otherwise be transmitted thereto from the OMT signal amplifier 3. By way of example, muscular actions, seismic activity and other mechanical motions and vibrations could introduce unwanted artifact noise to the alternating voltage biosignal produced by the sensing element 16. To this end, a minimum flexural rigidity depending upon the dimensions and material electricity of the ribbon assembly 5 are preferable in order to avoid the transmission of such mechanical forces to the piezo-active sensing element 16 via ribbon assembly 5.

To this end and by way of example only, the ideal thickness of the ribbon assembly is less than or equal to 25 microns, while the ideal width is about 4-8 mm. The ideal flexural rigidity of the flexible ribbon assembly 5 is less than or equal to $10 \times 10^{-4}$ lbs$^{-4}$-in$^4$. As indicated earlier, the flexible ribbon assembly 5 should be provided with slack or strain relief to avoid pulling on the OMT sensing element 16. That is, the length of the ribbon assembly 5 should ideally be at least 5% longer than the straight line distance between the piezo-active sensing element 16 and the amplifier 3 of the OMT sensor 1.

Figure 17:
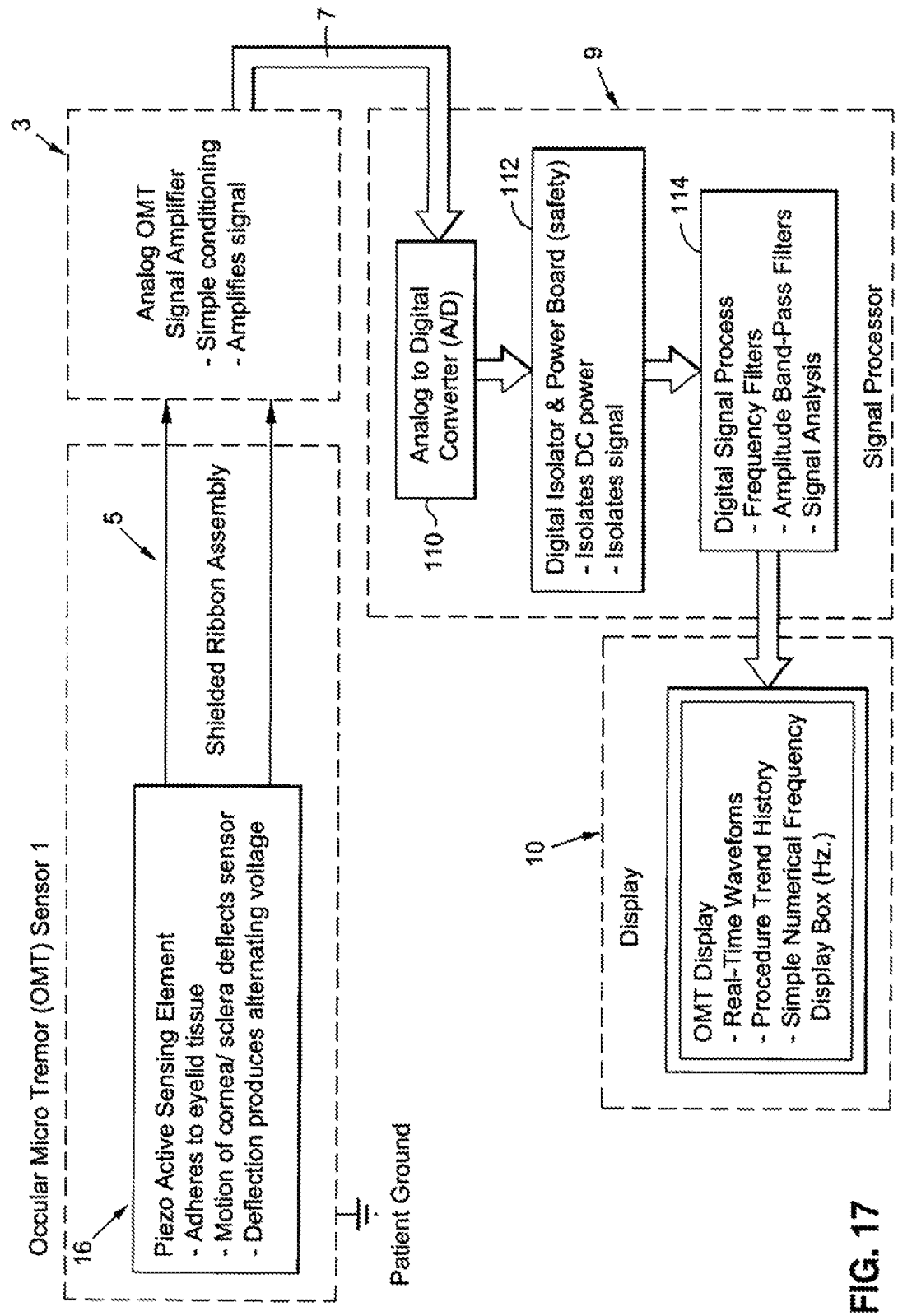
FIG. 17 is a block diagram illustration of a communication system in which the OMT sensor of FIG. 2 is coupled to a signal processor and to the display of FIG. 1.

FIG. 17 of the drawings shows the ocular micro tremor (OMT) sensor 1 of this invention connected to the previously mentioned signal processor 9. The processor 9 should be capable of filtering the amplified OMT biosignal and eliminating artifacts (such as those caused by gross eye movements and electrical or electromagnetic interference), analyzing the remaining signal and frequency information, and displaying the result at the display 10. More particularly, and as previously disclosed, the OMT alternating voltage biosignal generated in response to a deflection of the first and second piezoelectric films (30 and 34 of FIGS. 8-10) of the multiple layer piezo-active sensing element 16 is first supplied to and amplified by the OMT signal amplifier 3. One signal processor 9 which is suitable to be connected to the OMT signal amplifier 3 to receive the amplified biosignal and perform the aforementioned processor functions is shown and described in U.S. Pat. No. 7,011,410 issued Mar. 14, 2006, the details of which are incorporated herein by reference. Therefore, only a brief description of the signal processor 9 will be provided below.

The amplified alternating voltage OMT biosignal is supplied from the OMT signal amplifier 3 to an analog to digital (A/D) converter 110 of the signal processor 9 of FIG. 17 by the shielded cable 7 connected therebetween. The A/D converter 110 converts the analog alternating voltage biosignal to a digital signal to facilitate processing. The digital signal produced by A/D converter 110 is supplied to a digital isolator 112 which isolates the information content of the OMT biosignal from interference that might be produced by a source of power needed to drive the hardware required to perform the signal processing.

Frequency and amplitude bandpass filters 114 are used to provide the information to the anesthesiologist at the display 10 (of FIG. 1) which is connected to processor 9. By way of example, the filters 114 of processor 9 are adapted to recognize the input waveform generated by the piezo-active sensing element 16 of the OMT sensor 1. Any waveform having an amplitude greater than a predetermined threshold (such as that caused by microsaccades) are filtered and eliminated as not being representative of reliable OMT information.

A conventional processing technique (e.g., fast Fourier transform analysis, linear predictive modeling or peak counting) is used to compute the frequency of the digital OMT biosignal. In a peak counting approach, the OMT biosignal is sampled during a predetermined time interval. A count of the signal peaks is maintained and incremented during the sampling time. The peak frequency in numerical form (designated 14 in FIG. 1) is displayed by the display 10 (best shown in FIG. 1). Likewise, a real time graphical representation of the OMT signal waveform (designated 12 in FIG. 1) is also displayed so that a recent history of the patient's brain stem activity and level of consciousness is visually available at the display 10.

The frequency of the OMT biosignal being sampled is tested for validity so that spurious signals can be filtered and eliminated. For example, the frequency of the OMT biosignal can be inspected and compared with a predetermined frequency range that is known to conform to recognized physiological conditions. What is more, if the patient is subjected to a base line test prior to being anesthetized, the OMT biosignal can be compared with the base line test results. Any portion of the OMT biosignal which is determined to be indicative of gross eye movements and microsaccades is eliminated.

Figure 18:
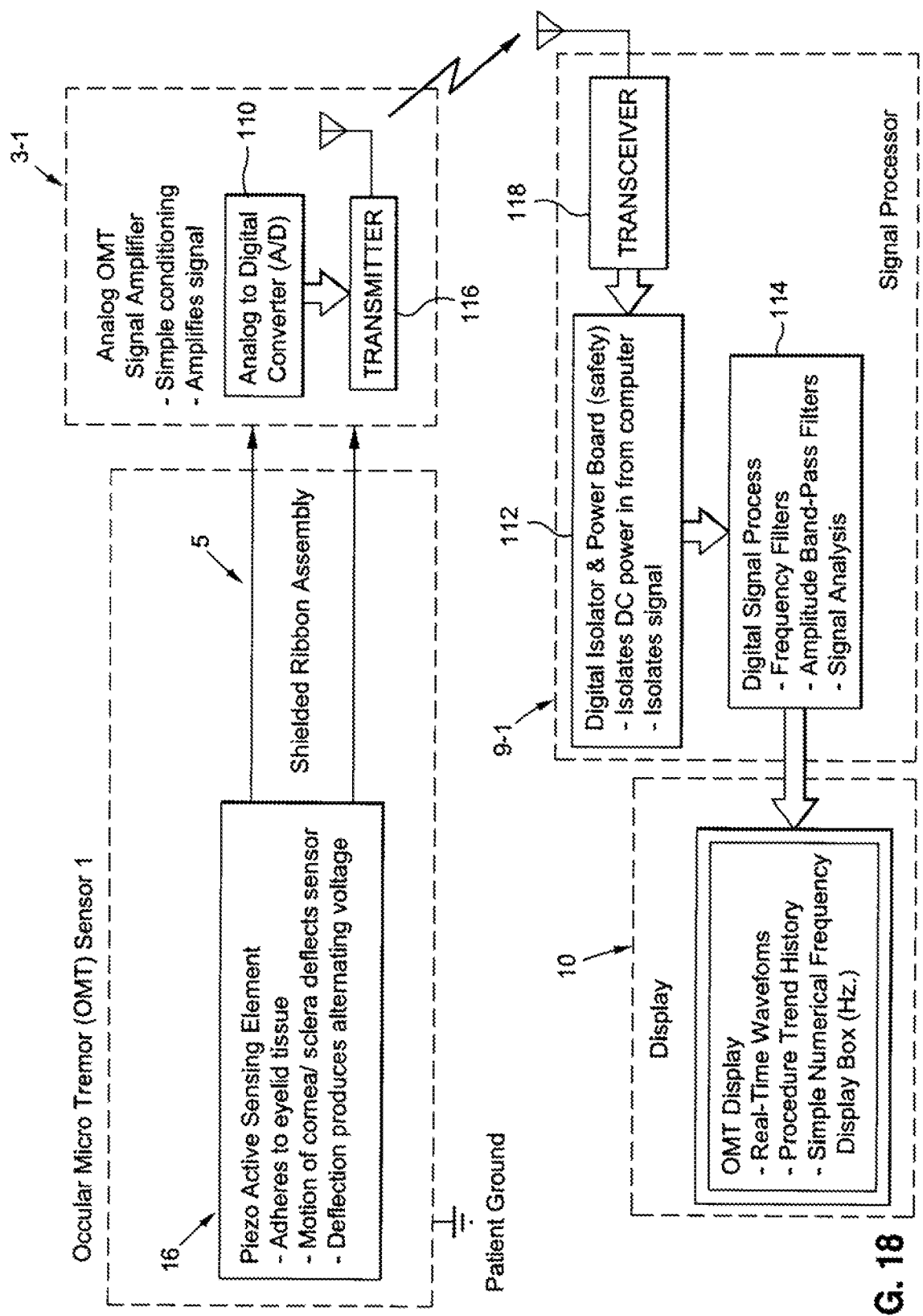
FIG. 18 is a block diagram illustration of a communication system in which the OMT sensor of FIG. 7 is coupled to a signal processor and to the display of FIG. 1 over a wireless communication path.

FIG. 18 of the drawings shows the piezo-active sensing element 16 of the OMT sensor 1 communicating with a signal processor 9-1 that is capable of receiving the amplified analog OMT biosignal from the OMT signal amplifier 3-1 over a wireless communication path. However, where the amplifier 3-1 communicates with the processor 9-1 over a wireless communication path, the previously described analog-to-digital converter 110 is removed from the processor (designated 9 in FIG. 17) and now located in the amplifier 3-1 to receive the OMT biosignal from the ribbon assembly 5. The A/D converter 110 of amplifier 3-1 of FIG. 18 is connected to a wireless transmitter 116 which is also located in the amplifier 3-1. In this case, the shielded cable (designated 7 in FIGS. 7 and 17) is eliminated. Likewise, the signal processor 9-1 of FIG. 18 is provided with a wireless transceiver 118 which is compatible to and capable of communicating with the wireless transmitter 116 of amplifier 3-1. Thus, the processor 9-1 may be located remotely from the OMT sensor 1 (e.g., at a nurses' station) so that the patient can be monitored as he recovers from an operation or other procedure and returns to consciousness.

Figure 19:
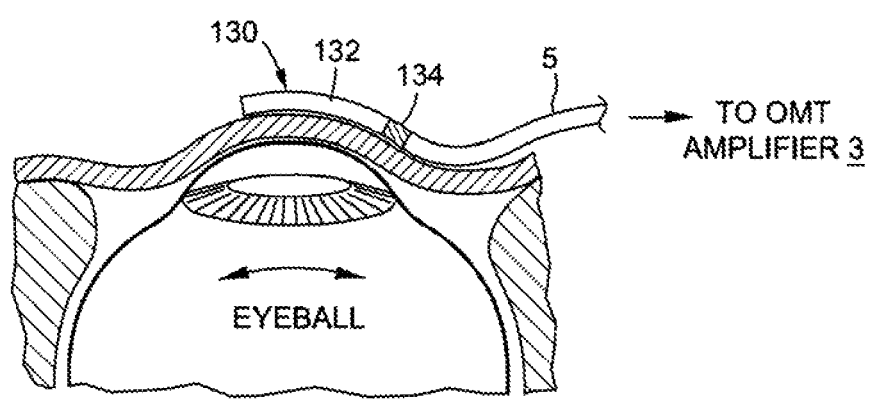
FIG. 19 shows another embodiment for an ocular micro tremor (OMT) sensor which includes a mechanical force transmitting arm actuator that is attached to the patient's eyelid at which to be deflected in response to micromotions of the patient's eyeball transmitted thereto so that an electrical biosignal can be generated by a piezo-active sensing element of the sensor.

It has been disclosed herein that the multiple layer piezo-active sensing element 16 of the ocular micro tremor (OMT) sensor 1 is attached to the eyelid of the individual being tested such that the sensing element 16 is deflected by the micromovements of an individual's eyeball to generate a biosignal. However, rather than having the micromovements applied from the individual's eyeball directly to the piezo-active sensing element 16 to cause a deflection thereof, the micromovements can instead be applied to an intermediate mechanical actuator. FIG. 19 of the drawings shows a modified ocular micro tremor (OMT) sensor 130 which includes a mechanical arm actuator 132 that is attached to the individual's eyelid so as to concentrate forces and stress on a relatively small piezo-active sensing element 134. In this case, the micromovements are applied from the eyeball to the mechanical arm actuator 132 rather than directly to the sensing element.

The mechanical arm actuator 132 of the modified OMT sensor 130 of FIG. 19 is preferably manufactured from a non-conductive medical grade plastic. The mechanical arm actuator 132 is attached to the individual's closed eyelid so as to conform to the shape of the eyelid at which to be deflected in response to the micromovements of the individual's eyeball. The piezo-active sensing element 134 of FIG. 19, which may be identical in construction to the sensing element 16 shown in FIGS. 8-10, is located between the mechanical arm actuator 132 and the flexible ribbon assembly 5. The flexible ribbon assembly 5 may be identical to that previously disclosed when referring to FIG. 13 and, therefore, the same reference numeral has been used therefor in FIG. 19. However, since it is now the lever advantage offered by the flexible mechanical arm actuator 132 of OMT sensor 130 which causes the piezo-active sensing element 134 to be deflected, the sensing element 134 can be made smaller and require less shielding when compared to the size and shielding associated with the sensing element 16. Moreover, the mechanical arm actuator 132 which is not subjected to electrical or electromagnetic interference need not be shielded.

The deflection of the mechanical arm actuator 132 in response to the micromovements of the individual's eyeball through the individual's eyelid below actuator 132 is transmitted to the adjacent piezo-active sensing element 134. The biosignal generated by the sensing element 134 is supplied to the amplifier (designated 3 in FIGS. 11 and 12) by way of the flexible ribbon assembly 5 as previously described.

Figure 20:
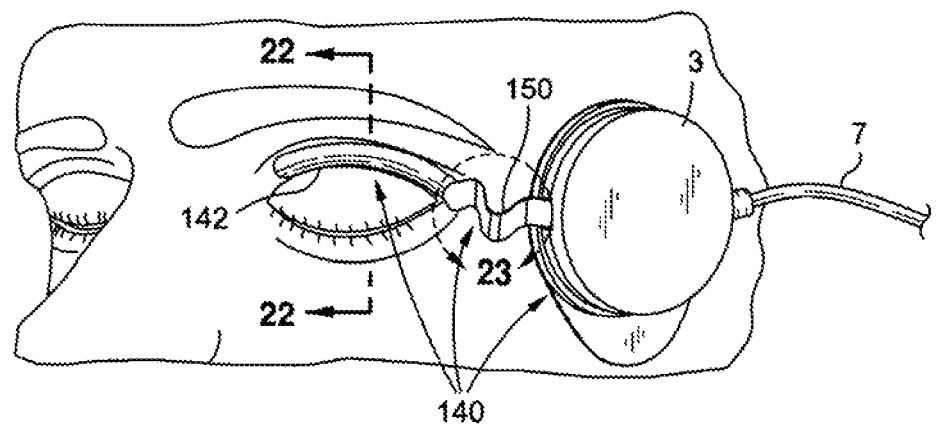
FIGS. 20-22 show a different embodiment for an ocular micro tremor (OMT) sensor having a tubular surface-mounted piezo-active sensing element that is located within the folds of the patient's eyelid at which to undergo a shape distortion in response to micromovements of the patient's eyeball transmitted thereto for generating an electrical biosignal.
Figure 21:
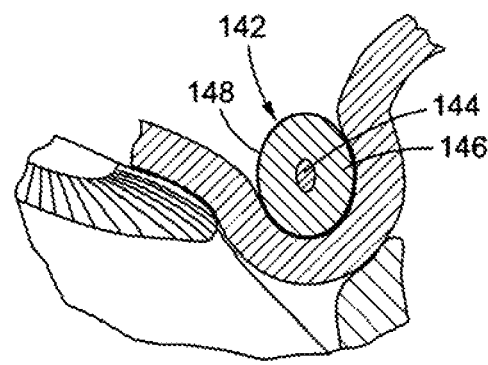

An ocular micro tremor (OMT) sensor 140 having a surface-mounted piezo-active sensing element 142 is described while referring concurrently to FIGS. 20-23 of the drawings. However, the piezo-active sensing element 142 of sensor 140 is a tubular sleeve rather than a pair of flexible planar films as in the case of piezo-active sensing element 16 of FIGS. 8-10. More particularly, the tubular sleeve sensing element 142 is subjected to having its original tubular shape distorted in order to generate a biosignal in response to the micromovements of the individual's eyeball. That is, as is best shown in FIG. 21, the tubular piezo-active sensing element 142 of OMT sensor 140 includes a flexible, electrically conductive interior area 144 which functions as a first electrical terminal. The electrically conductive interior area 144 of sensing element 142 is surrounded by a flexible intermediate piezoelectric material 146 that is adapted to be compressed and deformed. An electrically conductive exterior surface 148 surrounds the intermediate piezoelectric material 146. The electrically conductive outer surface 148 of the sensing element 142 which functions as a second electrical terminal may be surrounded by shielding material (not shown). By way of example only, each of the electrically conductive interior area 144 and exterior surface 148 (i.e., the first and second terminals) of the tubular piezo-active sensing element 142 of the OMT sensor 140 is manufactured from a thin electrically conductive metal mesh.

Figure 22:
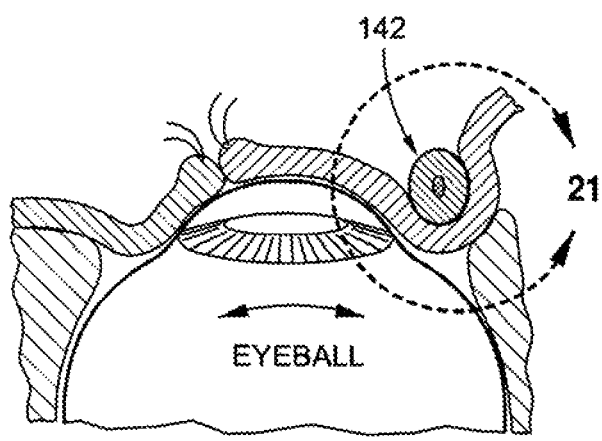

The tubular surface-mounted piezo-active sensing element 142 of the micro tremor sensor 140 is located in the folds of the individual's eyelid where it will be responsive to the micromovements of the individual's eyeball transmitted through the eyelid so as to undergo a compression and a deformation by which to generate a corresponding voltage. With the tubular piezo-active sensing element 142 initially in a relaxed state, the electrically conductive interior area 144 and exterior surface 148 as well as the intermediate piezoelectric material 146 lying therebetween all have a cylindrical configuration (not shown). However, when the tubular sensing element 142 receives a compressive force in response to micromovements of the individual's eyeball, the shape of each of the interior area 144, exterior surface 148 and intermediate piezoelectric material 146 is distorted and thereby assumes an elliptical configuration as shown in FIGS. 21 and 22.

The distortion and change of shape of the intermediate piezoelectrical material 146 produces a biosignal between the first and second terminals (i.e., the electrically conductive interior area 144 and the electrically conductive exterior surface 148) of the surface-mounted piezo-active sensing element 142. The biosignal generated by the sensing element 142 of the sensor 140 is supplied to the amplifier 3 by way of a tubular-to-planar strain relief adapter 150 (of FIG. 20) of the OMT sensor 140.

Figure 23:
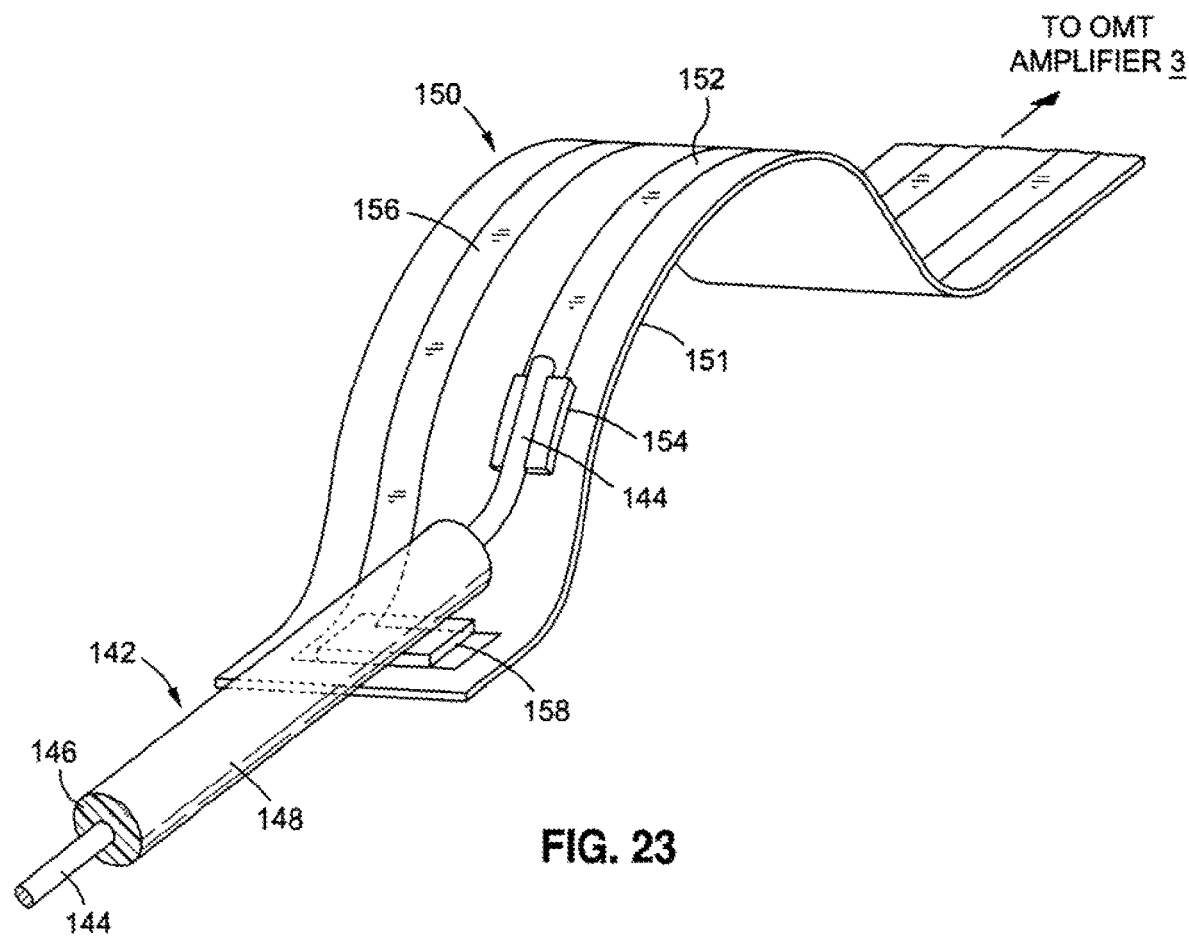
FIG. 23 is an enlarged detail of a tubular-to-planar strain relief adapter taken from the OMT sensor shown in FIG. 20.

Referring specifically to FIG. 23, details of the tubular-to-planar strain relief adapter 150 of the OMT sensor 140 of FIG. 20 are shown by which the electrical terminals 144 and 148 of the tubular piezo-active sensing element 142 are connected to the circuit board (designated 54 in FIG. 12) of amplifier 3 in substitution of the flexible ribbon assembly 3. The adapter 150 includes a flexible substrate 151 manufactured from a non-conductive material and having an arcuate (i.e., curved) configuration. The curved substrate 151 is adapted to be flexed in response to mechanical forces applied thereto to absorb pulling forces that could otherwise be applied to the piezo-active sensing element 142. A first electrically conductive trace 152 runs longitudinally along the substrate 151 from a first electrically conductive contact pad 154 to the amplifier 3. A second electrically conductive trace 156 runs longitudinally along the substrate 151 from a second electrically conductive contact pad 158 to the amplifier 3. The first and second electrically conductive traces 152 and 156 are arranged in spaced side-by-side parallel alignment along the non-conductive substrate 151 of adapter 150 so as to be electrically isolated from one another.

The electrically conductive inner area (i.e., the first terminal 144 of the tubular piezo sensing element 142 is connected (e.g., pushed into locking engagement) at a groove formed in the first contact pad 154 on substrate 151. The second contact pad 158 extends laterally across the substrate 151 so as to lie in front of and in axial alignment with the first contact pad 154. Therefore, at the same time that the inner conductive area 144 of the tubular piezo-active sensing element 142 contacts the first contact pad 154, the electrically conductive exterior surface (i.e., the second terminal) 148 of the tubular sensing element 142 will be automatically aligned to lie on and contact the second contact pad 158. Accordingly, when the tubular sensing element 142 undergoes a distortion and a change of its shape in response to micromovements of the individual's eyeball, the corresponding biosignal generated by the sensing element 142 between the first and second terminals 144 and 148 thereof is transmitted for amplification to the amplifier 3 by way of respective ones of the first and second conductive traces 152 and 156 of the strain relief adapter 150 which run along the substrate 151.

Figure 24:
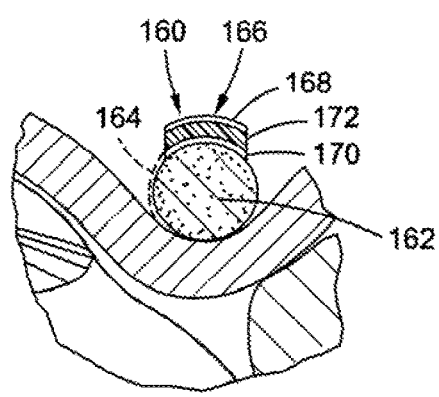
FIG. 24 shows yet another embodiment for an ocular micro tremor (OMT) sensor having a cylindrical force transmitting actuator that is located within the folds of the patient's eyelid at which to undergo a shape distortion in response to micromovements of the patient's eyeball transmitted thereto so that an electrical biosignal can be generated by a piezo-active sensing element of the sensor.

FIG. 24 of the drawings shows another embodiment for an ocular micro tremor (OMT) sensor 160 having a mechanical actuator and a piezo-active sensing element. Like the OMT sensor 130 that was described while referring to FIG. 19, the sensor 160 of FIG. 24 includes a mechanical force transmitting actuator that is responsive to the micromovements of the individual's eyeball. In this case, however, rather than an arm actuator attached to the individual's closed eyelid, a cylindrical force transmitting actuator 162 is located within the folds of the eyelid to lie closer to the eyeball than the piezo-active sensing element.

The cylindrical force transmitting actuator 162 of OMT sensor 160 is adapted to be compressed and undergo a deformation in response to the micromovements of the individual's eyeball transmitted through the individual's eyelid. In this regard, and by way of a first example, the cylindrical force transmitting actuator 162 is manufactured from a compressible material, such as a medical grade foam rubber, or the like. By way of a second example, the cylindrical force transmitting actuator 162 is filled with a compressible liquid, such as a gel, or the like. In the event that the cylindrical force transmitting actuator 162 is filled with liquid, the actuator is preferably surrounded by a flexible envelope 164 (shown in broken lines in FIG. 24).

The ocular micro tremor sensor 160 of FIG. 24 includes a flexible piezo-active sensing element 166 that is generally planar so as to be adhesively attached over and conform to the shape of the cylindrical force transmitting actuator 162. The sensing element 166 may be identical to the piezo-active sensing element 16 that was previously described while referring to FIGS. 8-10. However, to reduce the size of the sensor 160, the sensing element 166 that is shown in FIG. 24 includes an upper electrically conductive surface 168 which functions as a first terminal and a lower electrically conductive surface 170 which functions as a second electrical terminal. An intermediate piezoelectric material portion 172 is located between the upper and lower electrically conductive surfaces 168 and 170.

The micromovements of the individual's eyeball are applied through the individual's eyelid and result in a deformation and a change of shape of the cylindrical force transmitting actuator 162. The deformations of the cylindrical force transmitting actuator 162 are transmitted to the planar piezo-active sensing element 166 which lies over and against the force transmitting actuator 162. Accordingly, the intermediate piezoelectric material portion 172 of the sensing element 166 is correspondingly deflected so that a biosignal is produced between the first and second terminals (i.e., the upper and lower electrically conductive surfaces 168 and 170) lying at opposite sides of the piezoelectric material portion 172. The biosignal may then be supplied to an amplifier (like that designated 3 in FIGS. 11 and 12) by way of a flexible ribbon assembly (like that designated 5 in FIG. 13).

What is claimed is:

1. An apparatus comprising:
   a sensor comprising a piezoelectric element; and
   a flexible ribbon assembly comprising a conductive trace, wherein the conductive trace is coupled to the piezoelectric element;
   wherein the sensor is configured to conform to a shape of an eye register micro-movements of an eyeball having an amplitude in an inclusive range of 40 micrometers to 500 nanometers.

2. The apparatus of claim 1, wherein the sensor further comprises a conductive shield.

3. The apparatus of claim 1, wherein the sensor further comprises a conductive shield and an insulator, wherein the insulator insulates the conductive trace from the conductive shield.

4. The apparatus of claim 1, wherein the sensor further comprises a conductive shield and an insulator, wherein the insulator insulates the piezoelectric element from the conductive shield.

5. The apparatus of claim 1, wherein the piezoelectric element is 20 microns to 150 microns thick.

6. The apparatus of claim 1, wherein the piezoelectric element comprises Polyvinylidene fluoride.

7. The apparatus of claim 1, wherein the sensor further comprises an adhesive configured to attach to an eyelid.

8. The apparatus of claim 2, wherein the conductive shield comprises gold.

9. The apparatus of claim 1, wherein the sensor is further configured to register micro-movements of an eyeball having a frequency of 84 Hz.

10. The apparatus of claim 2, wherein the conductive shield is in electrical communication with the conductive trace.

11. An apparatus comprising:
   a sensor comprising:
   a sensing element comprising:
   a piezoelectric element; and
   an electrically conductive surface electrically coupled with the piezoelectric element; and
   an amplifier comprising a receptacle electrically coupled with the electrically conductive surface;
   wherein the sensor is configured to conform to a shape of an eye of a patient and to register micro-movements of an eyeball having an amplitude in an inclusive range of 40 micrometers to 500 nanometers.

12. The apparatus of claim 11, wherein the sensor further comprises a conductive shield.

13. The apparatus of claim 11, wherein the sensor further comprises a conductive shield and an insulator, wherein the insulator insulates the piezoelectric element from the conductive shield.

14. The apparatus of claim 11, wherein the piezoelectric element is 20 microns to 150 microns thick.

15. The apparatus of claim 11, wherein the piezoelectric element comprises Polyvinylidene fluoride.

16. The apparatus of claim 11, wherein the sensor further comprises an adhesive configured to attach to an eyelid.

17. The apparatus of claim 12, wherein the conductive shield comprises gold.

18. The apparatus of claim 11, wherein the sensor is further configured to register micro-movements of an eyeball having a frequency of 84 Hz.

19. The apparatus of claim 12, wherein the conductive shield is in electrical communication with the electrically conductive surface.

20. An apparatus comprising:
a sensor comprising a piezoelectric element; and
a conductor, wherein the conductor is electrically coupled to the piezoelectric element;
wherein the sensor is configured to conform to a shape of an eye; and the sensor is configured to register micro-movements of an eyeball having an amplitude in an inclusive range of 40 micrometers to 500 nanometers.

21. The apparatus of claim 20, wherein the sensor further comprises a conductive shield.

22. The apparatus of claim 20, wherein the sensor further comprises a conductive shield and an insulator, wherein the insulator insulates the piezoelectric element from the conductive shield.

23. The apparatus of claim 20, wherein the piezoelectric element is 20 microns to 150 microns thick.

24. The apparatus of claim 20, wherein the piezoelectric element comprises Polyvinylidene fluoride.

25. The apparatus of claim 20, wherein the sensor further comprises an adhesive configured to attach to an eyelid.

26. The apparatus of claim 21, wherein the conductive shield comprises gold.

27. The apparatus of claim 20, wherein the sensor is further configured to register micro-movements of an eyeball having a frequency of 84 Hz.

28. The apparatus of claim 21, wherein the conductive shield is in electrical communication with the conductor.

29. The apparatus of claim 1, wherein the conductive trace is in direct contact with the piezoelectric element.

30. The apparatus of claim 11, wherein the electrically conductive surface is in direct contact with the piezoelectric element.

31. The apparatus of claim 21, wherein the conductor is in direct contact with the piezoelectric element.

* * * * *